United States Patent
Kashima et al.

(10) Patent No.: US 10,413,369 B2
(45) Date of Patent: Sep. 17, 2019

(54) DEVICE, METHOD, AND SYSTEM FOR IMAGE GUIDED SURGICAL RESECTION

(71) Applicant: SONY CORPORATION, Tokyo (JP)

(72) Inventors: Koji Kashima, Kanagawa (JP); Tsuneo Hayashi, Tokyo (JP); Hisakazu Shiraki, Kanagawa (JP); Daisuke Tsuru, Chiba (JP); Takeshi Uemori, Tokyo (JP); Kentaro Fukazawa, Tokyo (JP); Yuki Sugie, Kanagawa (JP); Kenta Yamaguchi, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 39 days.

(21) Appl. No.: 15/566,790

(22) PCT Filed: May 6, 2016

(86) PCT No.: PCT/JP2016/063620
§ 371 (c)(1),
(2) Date: Oct. 16, 2017

(87) PCT Pub. No.: WO2016/185912
PCT Pub. Date: Nov. 24, 2016

(65) Prior Publication Data
US 2018/0353244 A1    Dec. 13, 2018

(30) Foreign Application Priority Data
May 19, 2015  (JP) .................................. 2015-101736

(51) Int. Cl.
*G06T 7/73* (2017.01)
*G06T 7/90* (2017.01)
(Continued)

(52) U.S. Cl.
CPC ................ *A61B 34/25* (2016.02); *A61B 1/04* (2013.01); *A61B 1/3132* (2013.01); *A61B 18/00* (2013.01);
(Continued)

(58) Field of Classification Search
None
See application file for complete search history.

(56) References Cited

U.S. PATENT DOCUMENTS 9,498,231 B2 *  11/2016  Haider ............... A61B 17/1703
2001/0055062 A1   12/2001  Shioda et al.
(Continued)

FOREIGN PATENT DOCUMENTS

JP      10-309281 A     11/1998
JP      2002-11022 A    1/2002
(Continued)

OTHER PUBLICATIONS

International Search Report dated Jul. 26, 2016 in PCT/JP2016/063620.

*Primary Examiner* — Jason A Pringle-Parker
(74) *Attorney, Agent, or Firm* — Oblon, McClelland, Maier & Neustadt, L.L.P.

(57) ABSTRACT

The present disclosure relates to an image processing device, an image processing method, and a surgical system with which more accurate surgical resection can be performed in a shorter time.
An identifying unit identifies the type of tissue degeneration in a mid-surgery image. In accordance with the identified type of the tissue degeneration, a drawing unit draws auxiliary information for the operator, the auxiliary information being to be superimposed on the mid-surgery image. The present disclosure can be applied to an endoscopic surgical system or the like that includes a display device, a camera
(Continued)

control unit (CCU), a light source device, a treatment tool device, a pneumoperitoneum apparatus, a recorder, a printer, an endoscope, an energetic treatment tool, forceps, trocars, a foot switch, and a patient's bed, for example.

12 Claims, 15 Drawing Sheets

(51) Int. Cl.

| | |
|---|---|
| *G06T 5/00* | (2006.01) |
| *G06T 5/50* | (2006.01) |
| *G06T 7/00* | (2017.01) |
| *G06T 7/20* | (2017.01) |
| *A61B 34/00* | (2016.01) |
| *A61B 1/04* | (2006.01) |
| *A61B 34/20* | (2016.01) |
| *A61B 90/00* | (2016.01) |
| *A61B 1/313* | (2006.01) |
| *A61B 18/00* | (2006.01) |
| *G06T 11/20* | (2006.01) |
| *A61B 17/00* | (2006.01) |

(52) U.S. Cl.
CPC .............. *A61B 34/20* (2016.02); *A61B 90/37* (2016.02); *G06T 5/006* (2013.01); *G06T 5/50* (2013.01); *G06T 7/0012* (2013.01); *G06T 7/20* (2013.01); *G06T 7/73* (2017.01); *G06T 7/90* (2017.01); *G06T 11/203* (2013.01); *A61B 2017/00973* (2013.01); *A61B 2018/00601* (2013.01); *A61B 2034/252* (2016.02); *A61B 2090/373* (2016.02); *G06T 2207/10068* (2013.01); *G06T 2207/20221* (2013.01); *G06T 2207/30004* (2013.01)

(56) References Cited

U.S. PATENT DOCUMENTS

| | | | | |
|---|---|---|---|---|
| 2002/0140694 | A1* | 10/2002 | Sauer | G06T 19/003 345/419 |
| 2006/0098010 | A1* | 5/2006 | Dwyer | G06T 169/006 634/424 |
| 2011/0160578 | A1* | 6/2011 | Tripathi | A61B 90/37 600/427 |
| 2013/0293578 | A1* | 11/2013 | Leung | G06F 3/147 345/633 |
| 2014/0024948 | A1 | 1/2014 | Shida et al. | |
| 2017/0281212 | A1* | 10/2017 | Asbun | A61B 10/02 |

FOREIGN PATENT DOCUMENTS

| | | |
|---|---|---|
| JP | 2004-24656 A | 1/2004 |
| JP | 2013-94173 A | 5/2013 |
| JP | 2013-192775 A | 9/2013 |
| WO | WO 2012/132790 A1 | 10/2012 |

* cited by examiner

DEVICE, METHOD, AND SYSTEM FOR IMAGE GUIDED SURGICAL RESECTION

TECHNICAL FIELD

The present disclosure relates to image processing devices, image processing methods, and surgical systems, and more particularly, to an image processing device, an image processing method, and a surgical system with which more accurate surgical resection can be performed in a shorter time.

BACKGROUND ART

In conventional surgery, in a case where resecting part of tissue including an affected area with a surgical knife or an energetic treatment tool, the operator determines a resection line in advance, and performs resection along the resection line. Therefore, the operator draws the resection line before the resection.

The method of drawing the resection line may be a method of adding a marker along the resection line on the tissue. Loss, disappearance, or blurring of the marker is undesirable, and therefore, the marking is performed by degenerating the tissue through burning with an energetic treatment tool or locally dyeing the tissue with a dye.

According to this method, to minimize the influence of the marking on the tissue, the marker is added not in the form of a continuous line but in the form of dots placed at intervals. Therefore, when performing resection, the operator needs to imagine a resection line connecting the marker dots from experience and judgment, and then perform the resection along the resection line. In doing so, the operator is required to make an accurate judgment, which puts a heavy burden on the operator. Also, in a case where the operator has poor experience or the like, a large number of markers are required, which leads to increases in influence on the tissue and surgical time.

To mark the resection line, there also is a method by which the blood vessels leading into the tissue including the affected area are compressed or ligated to block blood flow, and thus, the tissue is discolored. According to this method, the operator memorizes the discolored region, and performs resection by imagining a resection line surrounding the discolored region. In doing so, the operator is required to have a good memory, which puts a heavy burden on the operator.

Meanwhile, there is a fluorescent diagnostic device that detects from a fluorescent image the contour of an affected area and the contour of resected tissue including the affected area, and displays the distance between the contours on a monitor (see Patent Document 1, for example).

CITATION LIST

Patent Document

Patent Document 1: Japanese Patent Application Laid-Open No. 10-309281

SUMMARY OF THE INVENTION

Problems to be Solved by the Invention

As described above, in a case where an operator performs surgical resection, a heavy burden is put on the operator. Therefore, there is a demand for reduction of the burden on the operator by aiding judgment and memory of the operator, and for more accurate surgical resection in a short time.

The present disclosure is made in view of those circumstances, and aims to perform more accurate surgical resection in a shorter time.

Solutions to Problems

An image processing device of a first aspect of the present disclosure is an image processing device that includes: an identifying unit that identifies the type of tissue degeneration in a mid-surgery image; and a drawing unit that draws auxiliary information for the operator in accordance with the identified type of the tissue degeneration, the auxiliary information being to be superimposed on the mid-surgery image.

An image processing method of the first aspect of the present disclosure is compatible with the image processing device of the first aspect of the present disclosure.

In the first aspect of the present disclosure, the type of tissue degeneration in a mid-surgery image is identified, and auxiliary information for the operator is drawn in accordance with the identified type of the tissue degeneration, the auxiliary information being to be superimposed on the mid-surgery image.

It should be noted that the image processing device of the first aspect can also be formed by a computer executing a program.

Also, to obtain the image processing device of the first aspect, the program to be executed by the computer may be transmitted and provided via a transmission medium, or the program recorded on a recording medium may be provided.

A surgical system of a second aspect of the present disclosure is a surgical system that includes: a treatment device that degenerates the current object on which surgery is to be performed; an imaging device that generates a mid-surgery image of the current object; and an image processing device that performs image processing on the mid-surgery image. The image processing device includes: an identifying unit that identifies the type of tissue degeneration in the mid-surgery image; and a drawing unit that draws auxiliary information for an operator in accordance with the identified type of the tissue degeneration, the auxiliary information being to be superimposed on the mid-surgery image.

In the second aspect of the present disclosure, the current object on which surgery is to be performed is degenerated, a mid-surgery image of the current object is generated, and image processing is performed on the mid-surgery image. In the image processing, the type of tissue degeneration in the mid-surgery image is identified, and auxiliary information for the operator is drawn in accordance with the identified type of the tissue degeneration, the auxiliary information being to be superimposed on the mid-surgery image.

Effects of the Invention

According to the first and second aspects of the present disclosure, it is possible to perform more accurate surgical resection in a shorter time.

It should be noted that effects of the present technology are not limited to the effect described above, and may include any of the effects described in the present disclosure.

MODES FOR CARRYING OUT THE INVENTION

The following is a description of modes (hereinafter referred to as embodiments) for carrying out the present disclosure. It should be noted that explanation will be made in the following order.

1. First embodiment: endoscopic surgical system (FIGS. 1 through 10)
2. Second embodiment: endoscopic surgical system (FIGS. 11 through 13)
3. Explanation of a superimposing method (FIG. 14)
4. Explanation of a computer (FIG. 15)

First Embodiment (Example Configuration of a First Embodiment of an Endoscopic Surgical System)

Figure 1:
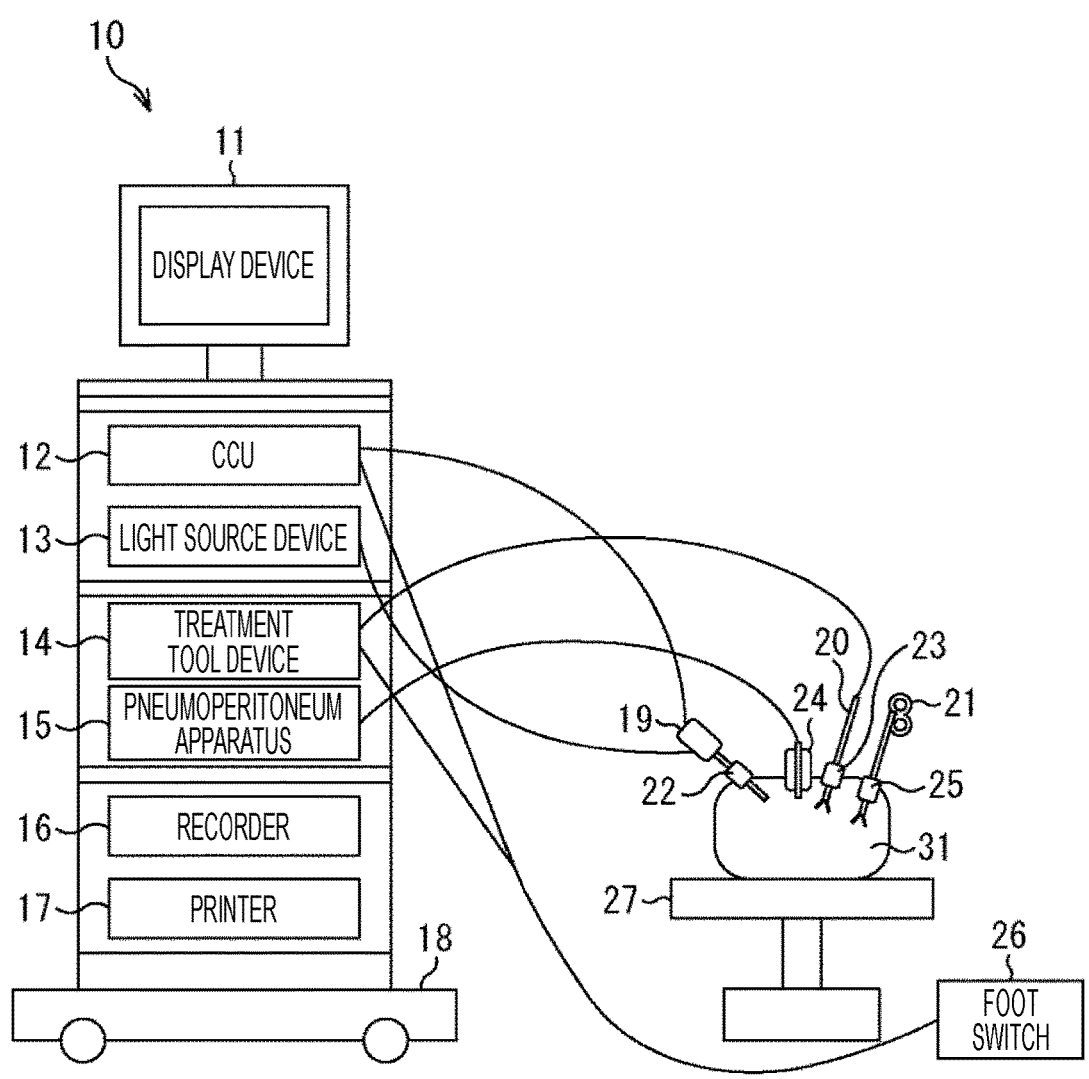
FIG. 1 is a diagram showing an example configuration of a first embodiment of an endoscopic surgical system to which the present disclosure is applied.

FIG. 1 is a diagram showing an example configuration of a first embodiment of an endoscopic surgical system to which the present disclosure is applied.

An endoscopic surgical system 10 includes a cart 18 on which a display device 11, a camera control unit (CCU) 12, a light source device 13, a treatment tool device 14, a pneumoperitoneum apparatus 15, a recorder 16, and a printer 17 are mounted. The endoscopic surgical system 10 also includes an endoscope (laparoscope) 19, an energetic treatment tool 20, forceps 21, trocars 22 through 25, a foot switch 26, and a patient's bed 27. The endoscopic surgical system 10 is installed in an operating room, for example, and aids the operator who is performing a laparoscopic operation on the affected area in an abdominal portion 31 of the patient lying on the patient's bed 27.

Specifically, the display device 11 of the endoscopic surgical system 10 is formed with a stationary 2D display, a head mount display, or the like. The display device 11 displays a mid-surgery image or the like supplied from the CCU 12.

The CCU 12 (image processing device) is connected to the endoscope 19 via a camera cable. Alternatively, the CCU 12 may be wirelessly connected to the endoscope 19. The CCU 12 receives a mid-surgery image that is generated by the endoscope 19 and is transmitted via the camera cable, and supplies the mid-surgery image to the display device 11. The CCU 12 supplies the received mid-surgery image to the recorder 16 and the printer 17, as necessary.

In accordance with an operation signal supplied from the foot switch 26, and using the mid-surgery image, the CCU 12 also detects a degenerated region that is a region of tissue degeneration in the mid-surgery image, and a degeneration method as the type of the tissue degeneration corresponding to the degenerated region. By a technique corresponding to the degeneration method, the CCU 12 draws a resection line in accordance with the degenerated region, and superimposes the resection line on the mid-surgery image. The CCU 112 supplies the mid-surgery image having the resection line superimposed thereon to the display device 11, and causes the display device 11 to display the mid-surgery image.

The light source device 13 is connected to the endoscope 19 via a light guide cable. The light source device 13 switches various kinds of light wavelengths, and emits light to the endoscope 19.

The treatment tool device 14 is a high-frequency output device, and is connected to the energetic treatment tool 20 and the foot switch 26 via cables. In accordance with an operation signal supplied from the foot switch 26, the treatment tool device 14 outputs a high-frequency current to the energetic treatment tool 20.

The pneumoperitoneum apparatus 15 includes an insufflation unit and a suction unit, and supplies air to the inside of the abdominal portion 31 through the hole of the trocar 24, which is a hole opener attached to the abdominal wall of the abdominal portion 31.

The recorder 16 records the mid-surgery image supplied from the CCU 12. The printer 17 prints out the mid-surgery image supplied from the CCU.

The endoscope 19 (imaging device) is formed with an imaging unit and an optical system such as an illuminating lens. The endoscope 19 is inserted into the abdominal portion 31, which is the current surgery subject, through the hole of the trocar 22 attached to the abdominal wall of the abdominal portion 31. The optical system of the endoscope 19 illuminates the inside of the abdominal portion 31 with light emitted from the light source device 13, and the imaging unit generates an image of the inside of the abdominal portion 31 as the mid-surgery image. The endoscope 19 supplies the mid-surgery image to the CCU 12 via the camera cable.

The energetic treatment tool 20 (treatment device) is formed with an electrical scalpel or the like. The energetic treatment tool 20 is inserted into the abdominal portion 31 through the hole of the trocar 23 attached to the abdominal wall of the abdominal portion 31. The energetic treatment tool 20 degenerates the inside of the abdominal portion 31 with electrical heat, or cuts the inside of the abdominal portion 31.

The forceps 21 are inserted into the abdominal portion 31 through the hole of the trocar 25 attached to the abdominal wall of the abdominal portion 31. The forceps 21 hold the inside of the abdominal portion 31. The endoscope 19, the energetic treatment tool 20, and the forceps 21 are held by the operator, an assistant, a scopist, a robot, or the like.

The foot switch 26 receives an action of a foot of the operator, an assistant, or the like. The foot switch 26 supplies the CCU 12 and the treatment tool device 14 with an operation signal indicating the received action.

The operator first presses the foot switch 26, and inputs a signal indicating that the mid-surgery image of the inside of the abdominal portion 31 imaged by the endoscope 19 is a mid-surgery image yet to be marked with the resection line. The operator then marks the resection line by degenerating at least part of the region including the affected area in the abdominal portion 31.

Examples of degeneration methods include a method by which the abdominal portion 31 is lightly burnt at intervals along the resection line with the energetic treatment tool 20 (this method will be hereinafter referred to as the burning method), a method by which the abdominal portion 31 is colored at intervals along the resection line with a dye (this method will be hereinafter referred to as the dyeing method), a method by which the blood vessels leading into the affected area of the abdominal portion 31 are compressed or ligated, to hinder the blood flow and thus discolor the affected area (this method will be hereinafter referred to as the discoloring method).

After marking the resection line, the operator presses the foot switch 26, and inputs a signal indicating that a mid-surgery image of the inside of the abdominal portion 31 to be imaged by the endoscope 19 thereafter will be a mid-surgery image marked with the resection line. As a result, the degenerated region and the degeneration method are detected by the CCU 12 using the mid-surgery images generated before and after the generation of the degenerated region marking the resection line, and the mid-surgery image on which the resection line is superimposed is displayed on the display device 11.

Looking at the resection line displayed on the display device 11, the operator cuts the abdominal portion 31 along the resection line with the energetic treatment tool 20 or the like, to resect the affected area in the abdominal portion 31.

As described above, using the endoscopic surgical system 10, the operator can resect the affected area in the abdominal portion 31, without performing laparotomy that involves cutting of the abdominal wall and opening of the abdominal portion 31. Furthermore, as the mid-surgery image having the resection line superimposed thereon is displayed on the display device 11, even an operator who has poor experience or the like can readily resect the affected area in the abdominal portion 31.

(Example Configuration of the CCU)

Figure 2:
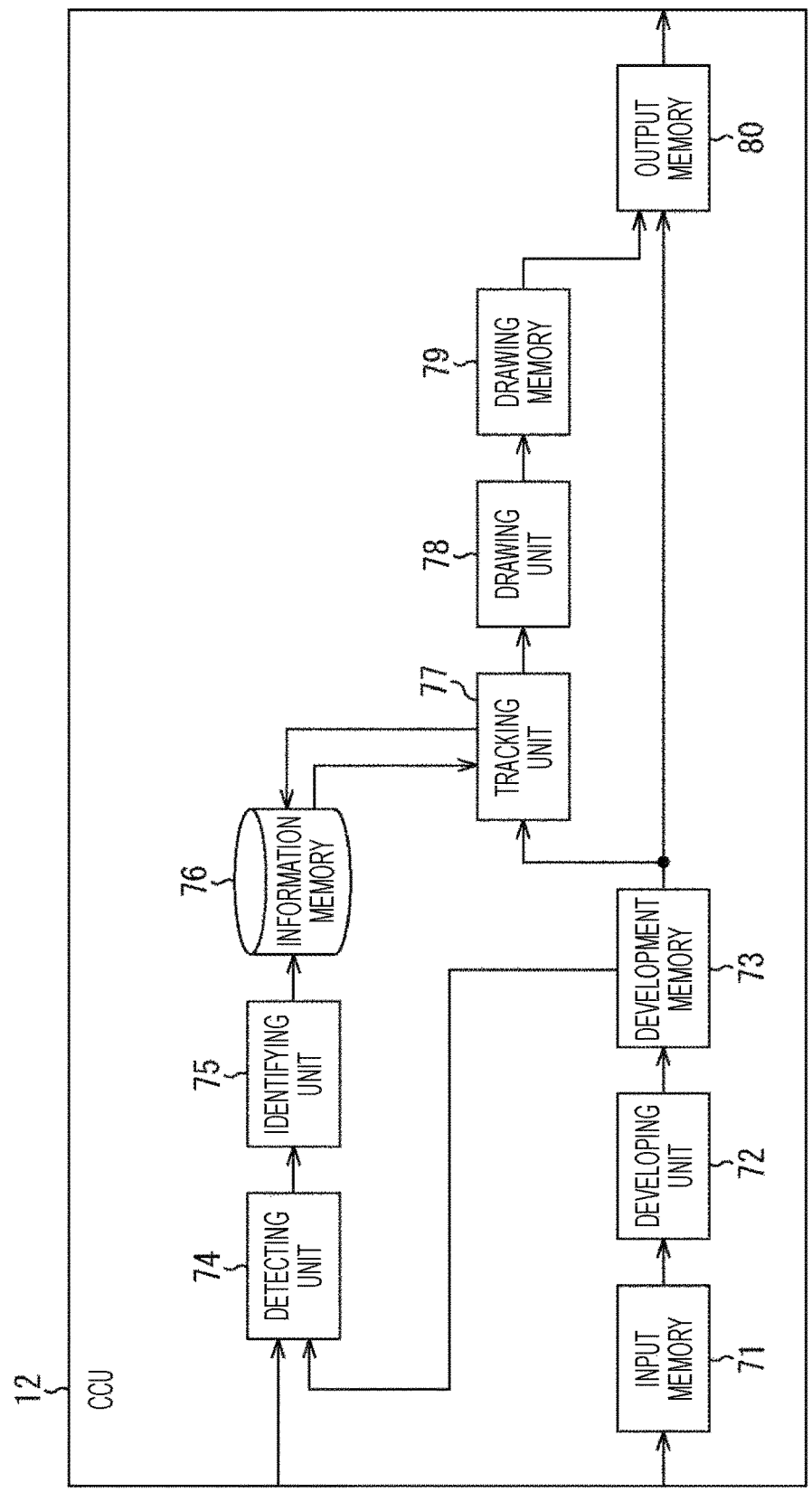
FIG. 2 is a block diagram showing an example configuration of the CCU in FIG. 1.

FIG. 2 is a block diagram showing an example configuration of the CCU 12 shown in FIG. 1.

The CCU 12 in FIG. 2 includes an input memory 71, a developing unit 72, a development memory 73, a detecting unit 74, an identifying unit 75, an information memory 76, a tracking unit 77, a drawing unit 78, a drawing memory 79, and an output memory 80.

A mid-surgery image transmitted from the endoscope 19 is input to the input memory 71. The input memory 71 stores the input mid-surgery image. The input memory 71 also reads out the stored mid-surgery image, and supplies the mid-surgery image to the developing unit 72.

The developing unit 72 performs a development process on the mid-surgery image supplied from the input memory 71, and supplies the developed mid-surgery image to the development memory 73. The development memory 73 stores the mid-surgery image supplied from the developing unit 72. The development memory 73 also reads out the stored mid-surgery image, and supplies the mid-surgery image to the tracking unit 77 and the output memory 80.

The detecting unit 74 acquires an operation signal that is supplied from the foot switch 26 and indicates an action of the operator on the foot switch 26 immediately before the start of degeneration. In accordance with the operation signal, the detecting unit 74 reads the mid-surgery image from the development memory 73, and sets the mid-surgery image as the mid-surgery image generated immediately before generation of a degenerated region (this mid-surgery image will be hereinafter referred to as the pre-degeneration image).

The detecting unit 74 also acquires an operation signal that is supplied from the foot switch 26 and indicates an action of the operator on the foot switch 26 immediately after the end of the degeneration. In accordance with the operation signal, the detecting unit 74 reads the mid-surgery image from the development memory 73, and sets the mid-surgery image as the mid-surgery image generated immediately after the generation of the degenerated region (this mid-surgery image will be hereinafter referred to as the post-degeneration image). In accordance with changes in color and luminance between the pre-degeneration image and the post-degeneration image, the detecting unit 74 detects the degenerated regions in the post-degeneration image.

Specifically, the detecting unit 74 first detects the motion vector between the pre-degeneration image and the post-degeneration image, and performs motion compensation, to cancel out movement of the endoscope 19 and the object. In a case where adequate motion compensation cannot be performed only through movement in the horizontal direction and the vertical direction of the pre-degeneration image or the post-degeneration image, the detecting unit 74 also performs motion compensation by rotating and rescaling the pre-degeneration image or the post-degeneration image through affine transform.

The detecting unit 74 then calculates differences in color and luminance between the pre-degeneration image and the post-degeneration image subjected to the position correction using motion compensation, and detects regions having larger differences in color and luminance than threshold values. The detecting unit 74 then deletes regions having smaller areas among the detected regions, and sets the remaining regions as the degenerated regions.

In the above manner, the detecting unit 74 detects the degenerated regions in accordance with differences in color and luminance between the pre-degeneration image and the post-degeneration image. Therefore, to increase detection accuracy, it is preferable not to move the endoscope 19 before and after the marking of the resection line. It should be noted that, the detecting unit 74 may detect degenerated regions in accordance not only with differences in color and luminance between the pre-degeneration image and the post-degeneration image, but also with image information such as luminance gradients and edges in the pre-degeneration image and the post-degeneration image.

The detecting unit 74 supplies the identifying unit 75 with feature information such as the shape, the amount of change in luminance, the amount of change in color, the edge pattern, and the texture of each degenerated region, information about the feature points that are designed for identifying each degenerated region and are located around each degenerated region, location information indicating the locations in the post-degeneration image, and the number of degenerated regions.

In accordance with the feature information about each degenerated region and the number of degenerated regions supplied from the detecting unit 74, the identifying unit 75 identifies the degeneration method of the degenerated regions. The identification technique may be identification using threshold values, pattern matching, machine learning, or the like. The identifying unit 75 supplies the information memory 76 with degenerated region information about degenerated regions. The degenerated region information includes degenerated region identification information including the edge pattern and the texture of each degenerated region or information about the feature points around the degenerated region, the degeneration method, the location information, the shape, and the number of degenerated regions.

The information memory 76 stores the degenerated region information supplied from the identifying unit 75. The information memory 76 also updates the stored degenerated region information with degenerated region information supplied from the tracking unit 77. The information memory 76 reads out the stored degenerated region information, and supplies the degenerated region information to the tracking unit 77.

The tracking unit 77 supplies the drawing unit 78 with the degeneration method, the location information, and the shape of each degenerated region, and the number of degenerated regions included in the degenerated region information supplied from the information memory 76. In accordance with the degenerated region identification information and the location information included in the degenerated region information, the tracking unit 77 also detects the degenerated regions in a mid-surgery image that is supplied from the development memory 73 and is generated later than the mid-surgery image corresponding to the degenerated region information. That is, in accordance with the degenerated region identification information and the location information, the tracking unit 77 tracks temporal changes in the degenerated regions in the mid-surgery image generated after the degenerated region generation. The tracking unit 77 supplies the information memory 76 with degenerated region information about the detected degenerated regions.

In accordance with the degeneration method, the location information, and the shape of each degenerated region, and the number of degenerated regions supplied from the tracking unit 77, the drawing unit 78 draws a resection line and the like, and generates a resection line image as auxiliary information for the operator. Therefore, the resection line image changes over time in accordance with temporal changes in the degenerated regions tracked by the tracking unit 77.

Alternatively, the drawing unit 78 may draw a resection that is the average of the resection line determined from the degeneration method, the location information, and the shape of each degenerated region, and the number of degenerated regions, and a resection line defined at an earlier time than the resection line, and then generate a resection line image. In this case, a rapid resection line change can be prevented.

The drawing unit 78 supplies the resection line image to the drawing memory 79. The drawing memory 79 stores the resection line image supplied from the drawing unit 78. The drawing memory 79 reads out the stored resection line image, and supplies the resection line image to the output memory 80.

The output memory 80 stores the mid-surgery image supplied from the development memory 73. When the resection line image corresponding to the stored mid-surgery image is supplied, the output memory 80 also writes the resection line image over the stored mid-surgery image. That is, the output memory 80 draws the resection line over the mid-surgery image. The output memory 80 reads out the stored mid-surgery image having the resection line superimposed thereon or the stored mid-surgery image having no resection line superimposed thereon, and transmits the mid-surgery image to the display device 11.

As described above, the CCU 12 tracks temporal changes in degenerated regions. Accordingly, even in a case where the degenerated regions in a mid-surgery image change over time, an appropriate resection line can be superimposed on the mid-surgery image. Thus, in a case where a degenerated region is deleted from a mid-surgery image due to execution of resection or movement of the endoscope 19, for example, it is possible to prevent unnecessary display of the resection line corresponding to the degenerated region.

(Explanation of a Resection Line in a Case where the Degeneration Method is the Burning Method)

Figure 3:
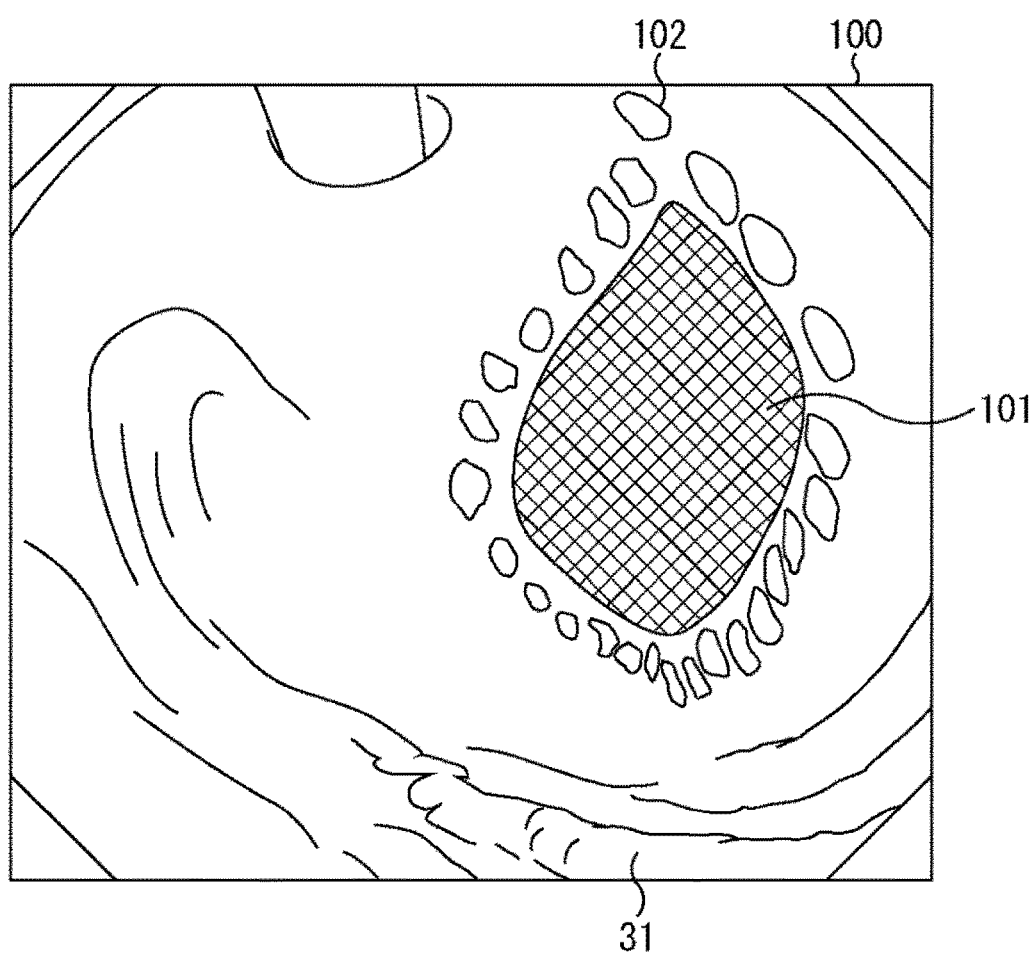
FIG. 3 is a diagram showing an example of a post-degeneration image in a case where the degeneration method is a burning method.

FIG. 3 is a diagram showing an example of a post-degeneration image in a case where the degeneration method is the burning method.

In the example shown in FIG. 3, the abdominal portion 31 is the stomach. As shown in FIG. 3, in a case where the abdominal portion 31 is degenerated by the burning method, degenerated regions 102 (26 degenerated regions in the example shown in FIG. 3) exist in a dot-line pattern, surrounding an affected area 101 of the inner wall of the abdominal portion 31 in a post-degeneration image 100.

Figure 4:
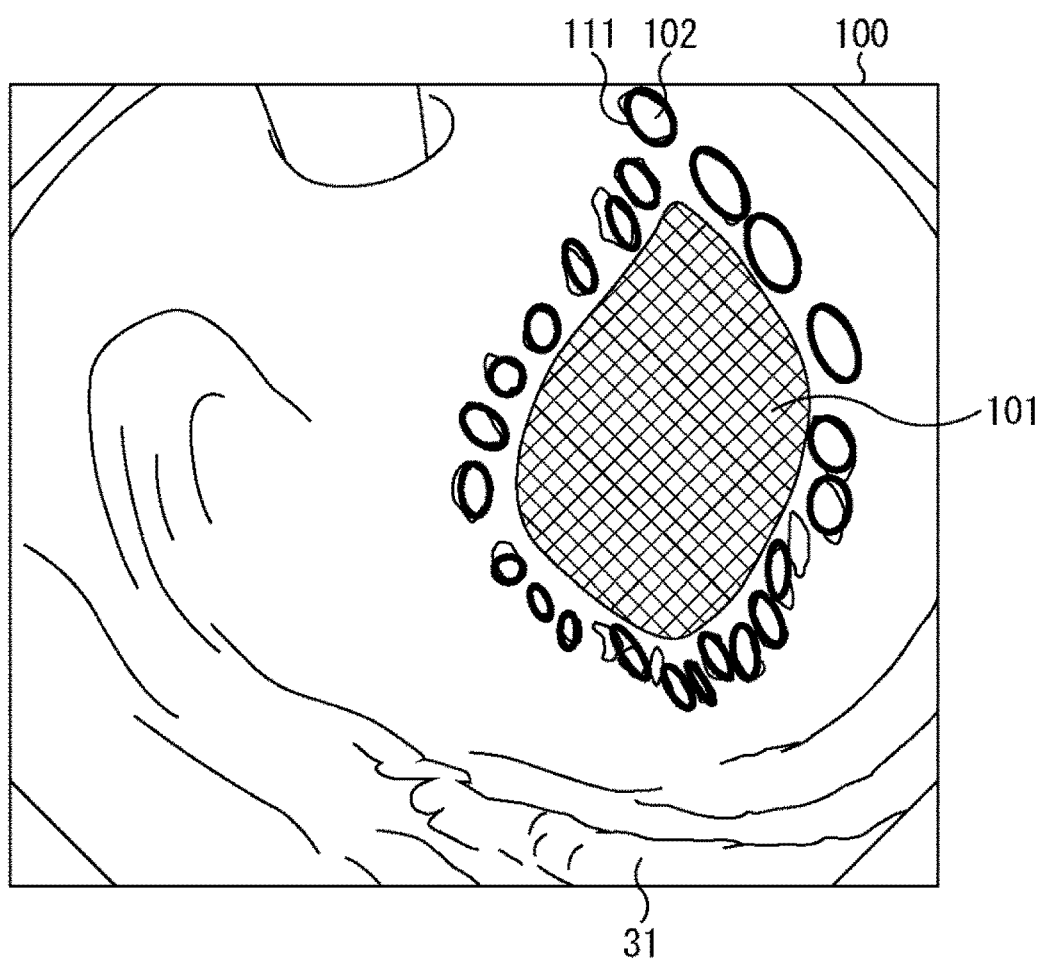
FIG. 4 is a diagram showing an example of degenerated regions detected in a case where the degeneration method is the burning method.

In this case, as shown in FIG. 4, the detecting unit 74 detects circular regions 111 (23 circular regions in the example in FIG. 4) including at least part of the degenerated regions 102, in accordance with a pre-degeneration image not showing the degenerated regions 102 and the post-degeneration image 100.

Also, since the regions 111 have small circular shapes as indicated by the feature information about the degenerated regions 102, and the number of the regions 111 is larger than one, for example, the identifying unit 75 determines the degeneration method of the degenerated regions to be the burning method.

Figure 5:
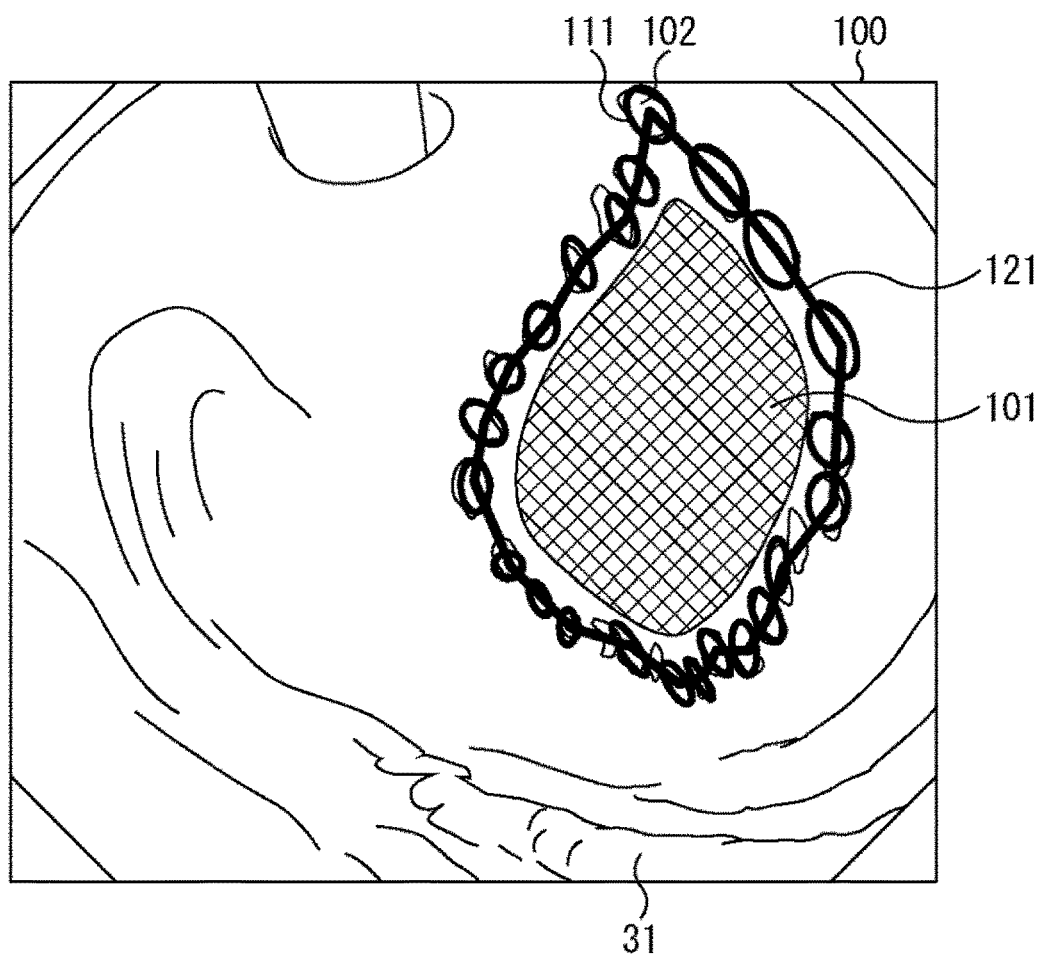
FIG. 5 is a diagram showing a first example of a resection line in a case where the degeneration method is the burning method.

As shown in FIG. 5, in accordance with the fact that the degeneration method is the burning method as indicated by the degenerated region information about the regions 111, the location information and the shape of each degenerated region, and the number of the degenerated regions, the drawing unit 78 then draws a resection line 121 that extends through the gravity centers of all the regions 111 in the post-degeneration image 100, for example. As a result, the post-degeneration image 100 on which the resection line 121 is superimposed is generated at the output memory 80.

The resection line 121 may be a straight line or a curved line, and may or may not be the shortest path that extends through all the regions 111. Alternatively, the drawing unit 78 may extract the discolored portions of the tissue of the affected area 101 or the abdominal portion 31 from the post-degeneration image 100, and draw the resection line 121 so that the discolored portions are included in the region surrounded by the resection line 121.

Figure 6:
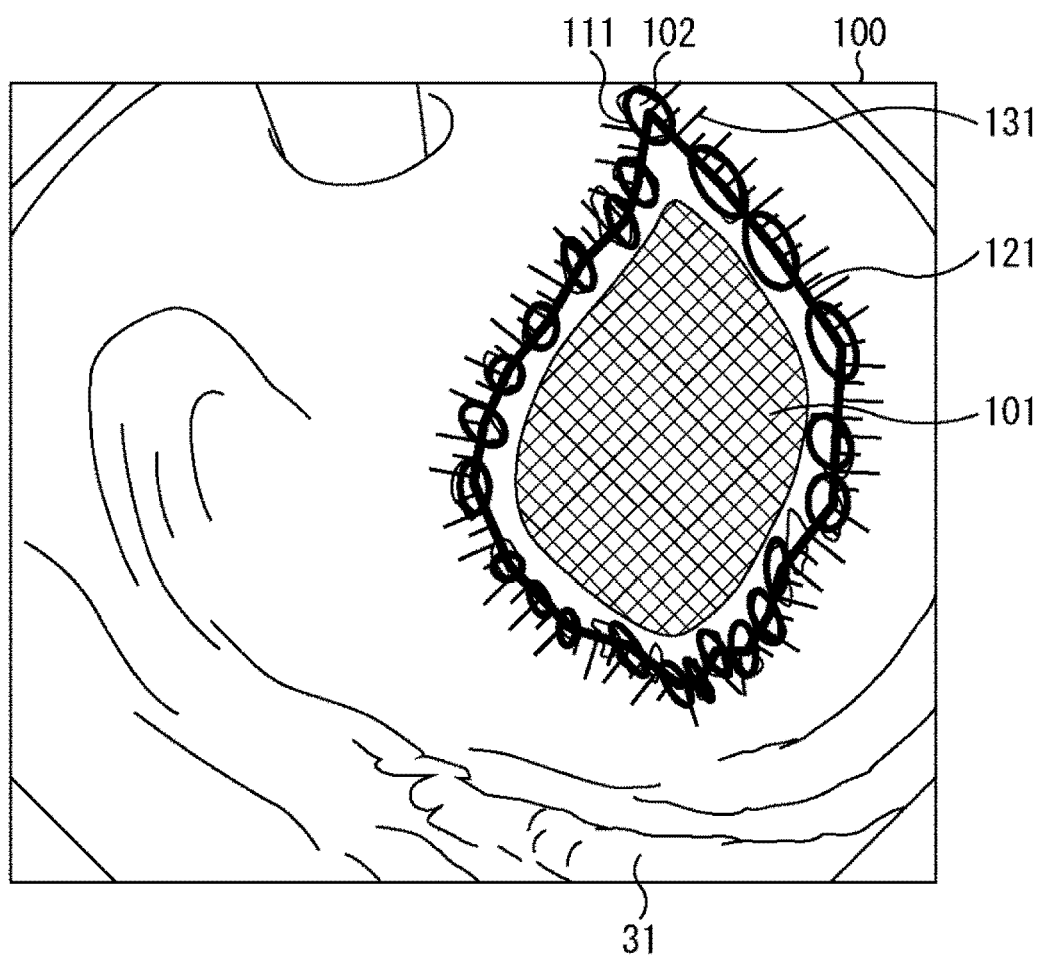
FIG. 6 is a diagram showing a second example of a resection line in a case where the degeneration method is the burning method.

Also, as shown in FIG. 6, the drawing unit 78 may add scale marks 131 to the resection line 121. In this case, the operator can easily know the distances between the regions 111.

Figure 7:
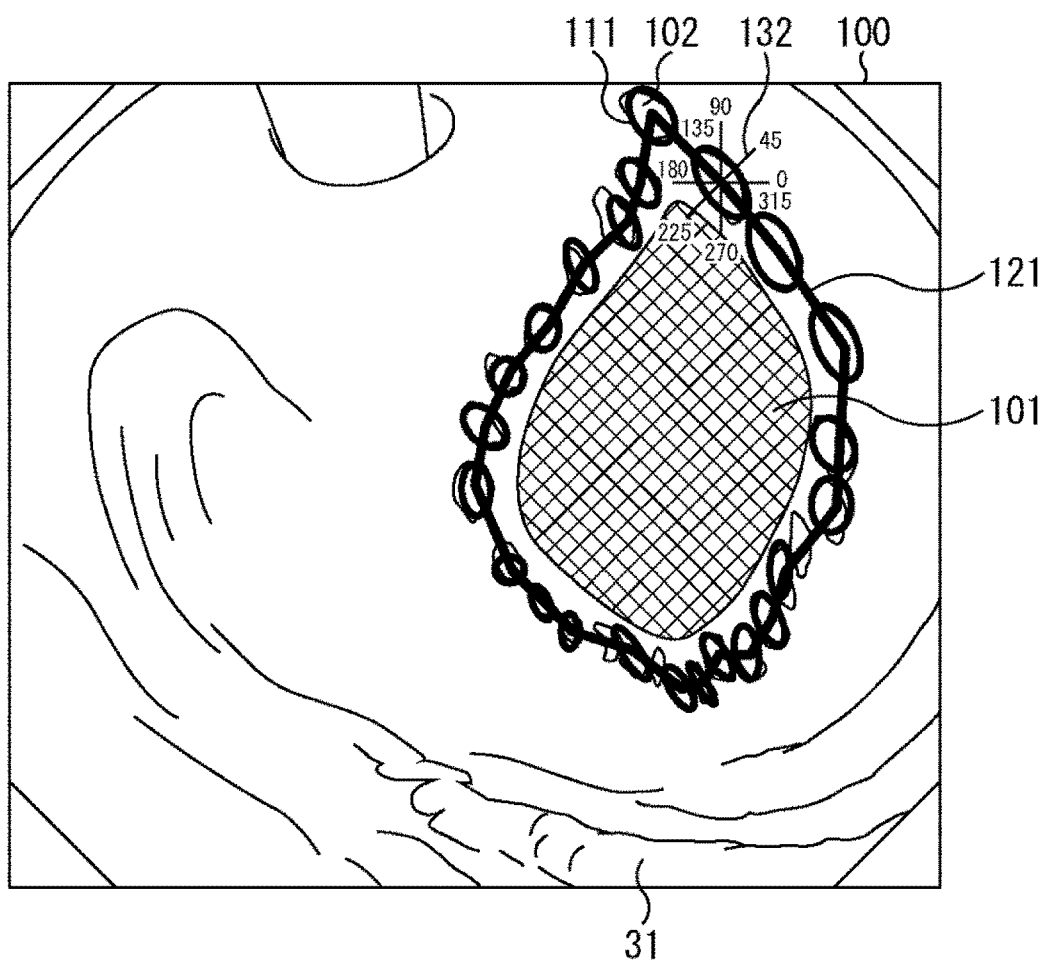
FIG. 7 is a diagram showing a third example of a resection line in a case where the degeneration method is the burning method.

Further, as shown in FIG. 7, the drawing unit 78 may draw not only the resection line 121 but also lines 132 (four lines in the example in FIG. 7) that are radial lines radiating from the gravity center of each region 111 and indicate angles to the horizontal direction. In this case, the operator can easily know the angles formed by the resection line 121 between the regions 111. It should be noted that, in the example shown in FIG. 7, only the line 132 drawn on one region 111 is shown, for ease of explanation.

Figure 8:
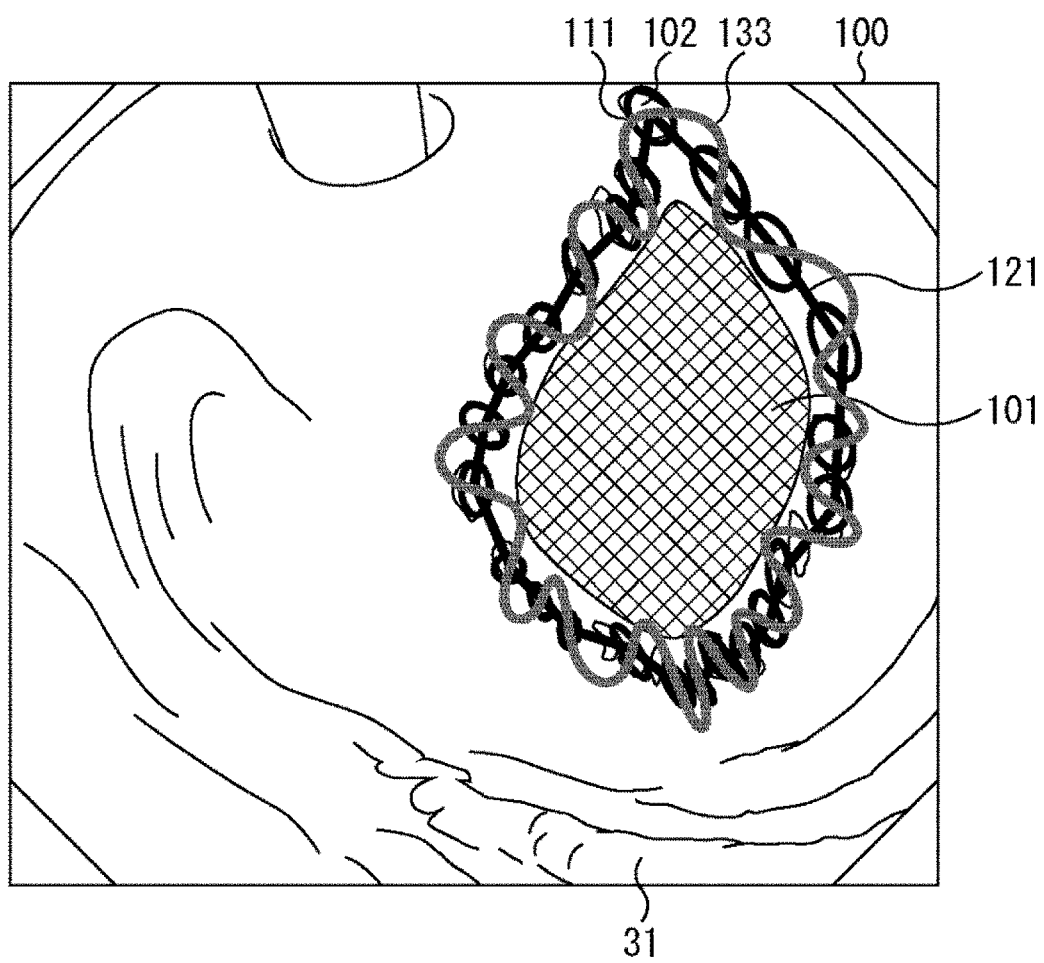
FIG. 8 is a diagram showing a fourth example of a resection line in a case where the degeneration method is the burning method.

Also, as shown in FIG. 8, the drawing unit 78 may draw not only the resection line 121 but also a resection line 133 by a different path determination method from that for the resection line 121. In this case, the operator presses the foot switch 26, and selects one of the resection lines 121 and 133 displayed on the display device 11. By doing so, the operator selects the path determination method corresponding to the selected resection line 121 or 133. After the operator selects the path determination method, the drawing unit 78 draws only one resection line according to the selected path determination method.

(Explanation of a Resection Line in a Case where the Degeneration Method is the Discoloring Method)

Figure 9:
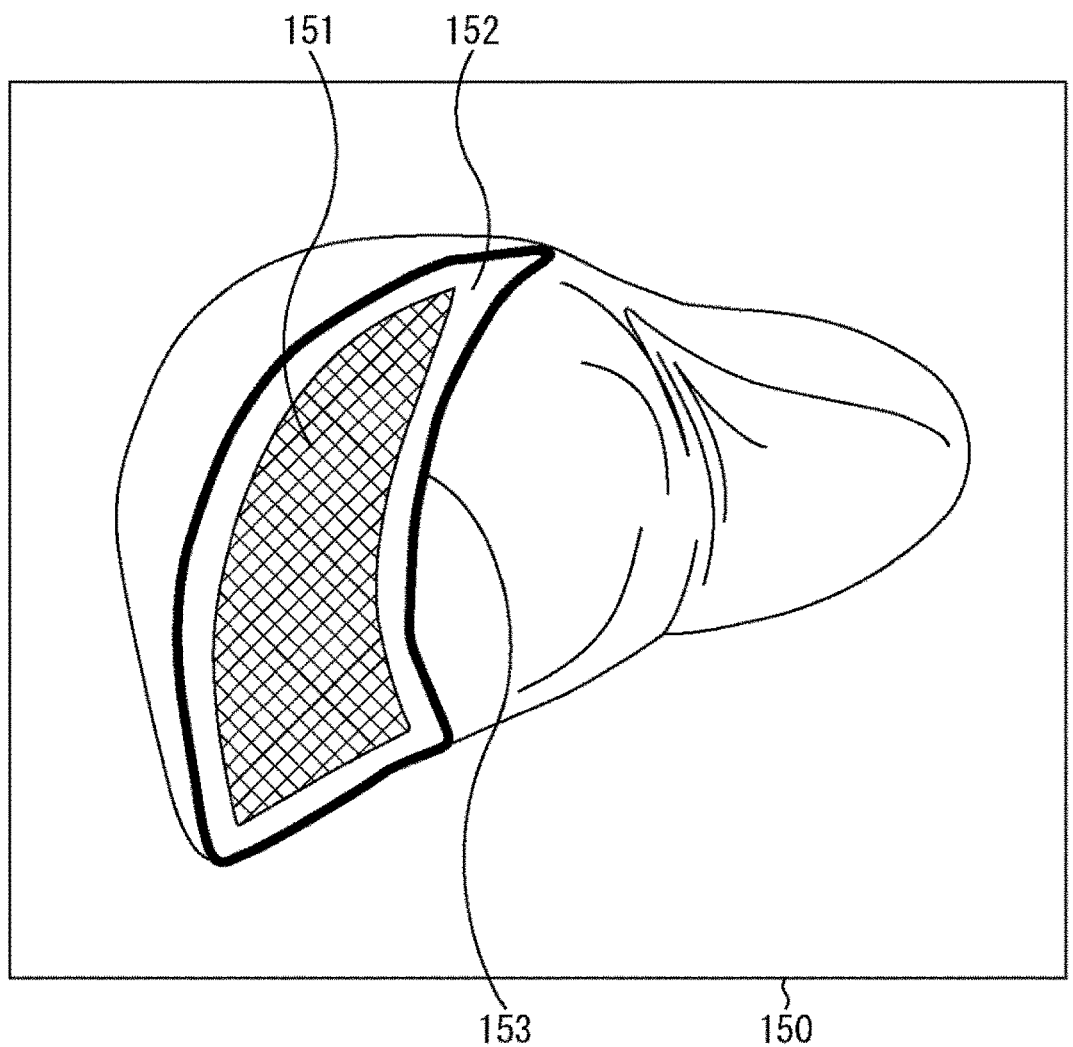
FIG. 9 is a diagram showing an example of a resection line in a case where the degeneration method is a discoloring method.

FIG. 9 is a diagram showing an example of a resection line in a case where the degeneration method is the discoloring method.

In the example shown in FIG. 9, the abdominal portion 31 is the liver. As shown in FIG. 9, in a case where the abdominal portion 31 is degenerated by the discoloring method, the detecting unit 74 detects a degenerated region 152 that is the front section of the abdominal portion 31 including an affected area 151 in a post-degeneration image 150, for example.

Also, since the degenerated region 152 has a large shape as indicated by the feature information about the degenerated region 152, and there is only one degenerated region 152, for example, the identifying unit 75 determines the degeneration method of the degenerated region to be the discoloring method.

As shown in FIG. 9, in accordance with the fact that the degeneration method is the discoloring method as indicated by the degenerated region information about the degenerated region 152, and the location information and the shape of each degenerated region, the drawing unit 78 then draws a resection line 153 indicating the contour of the degenerated region 152 in the post-degeneration image 150. As a result, the post-degeneration image 150 on which the resection line 153 is superimposed is generated at the output memory 80.

It should be noted that the drawing unit 78 may add scale marks to the resection line 153 as in the case shown in FIG. 6. Alternatively, the drawing unit 78 may draw not only the resection line 153 but also radial lines radiating from a predetermined point on the resection line 153 serving as the center point, as in the case shown in FIG. 7.

(Explanation of a Process to be Performed by the CCU)

Figure 10:
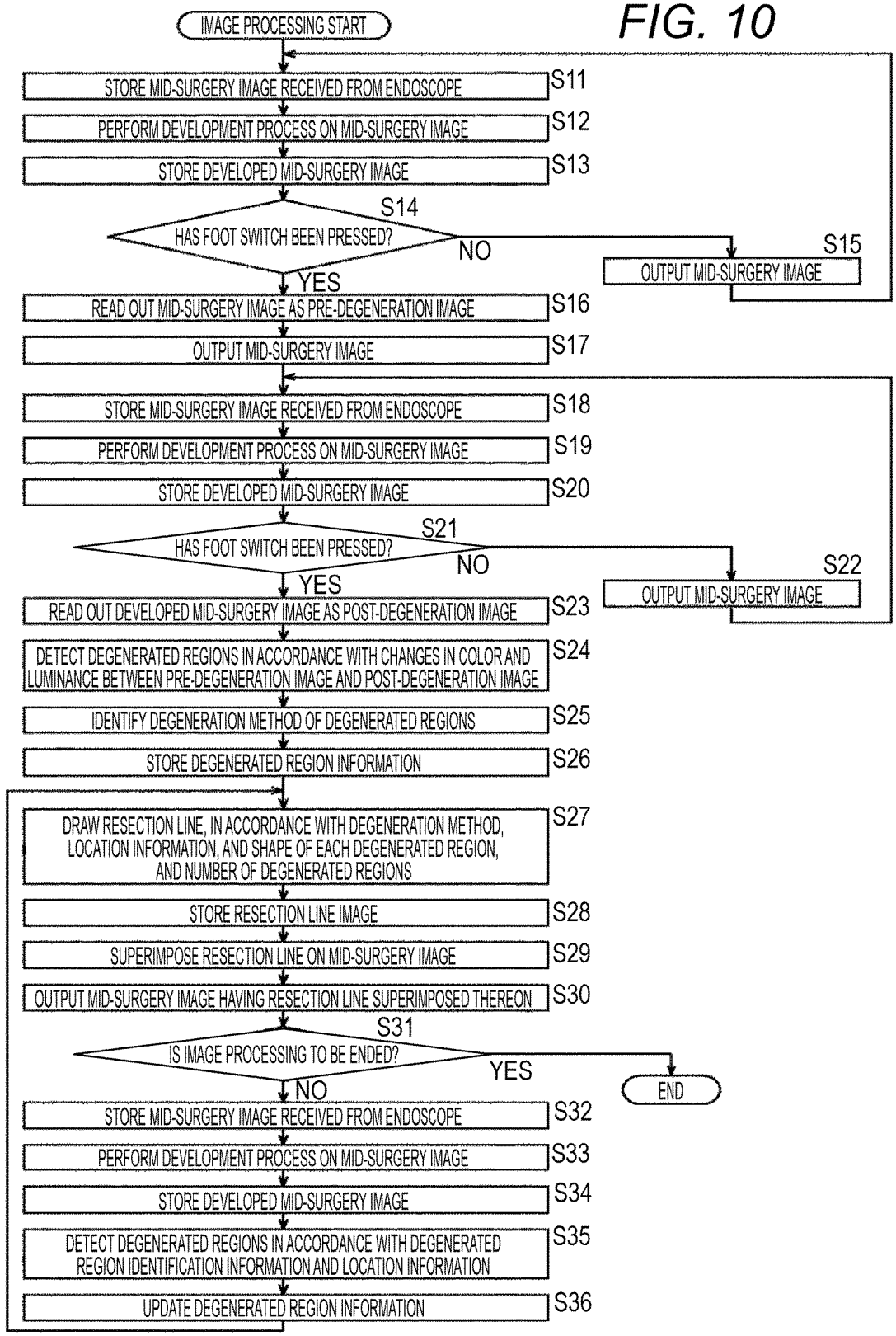
FIG. 10 is a flowchart for explaining image processing to be performed by the CCU shown in FIG. 2.

FIG. 10 is a flowchart for explaining image processing to be performed by the CCU 12 shown in FIG. 2.

In step S11 in FIG. 10, the input memory 71 stores a mid-surgery image received from the endoscope 19. The input memory 71 also reads out the stored mid-surgery image, and supplies the mid-surgery image to the developing unit 72.

In step S12, the developing unit 72 performs a development process on the mid-surgery image supplied from the input memory 71, and supplies the developed mid-surgery image to the development memory 73.

In step S13, the development memory 73 stores the developed mid-surgery image supplied from the developing unit 72. The development memory 73 also reads out the stored mid-surgery image, and supplies the mid-surgery image to the tracking unit 77 and the output memory 80. The output memory 80 stores the mid-surgery image supplied from the development memory 73.

In step S14, the detecting unit 74 determines whether the foot switch 26 has been pressed by the operator or the like, or whether an operation signal has been acquired from the foot switch 26. If it is determined in step S14 that the foot switch 26 has not been pressed yet, the process moves on to step S15.

In step S15, the output memory 80 outputs the stored mid-surgery image to the display device 11. As a result, the mid-surgery image is displayed on the display device 11. After the procedure in step S15, the process returns to step S11, and the procedures insteps S11 through S15 are repeated until the foot switch 26 is pressed.

If it is determined in step S14 that the foot switch 26 has been pressed, on the other hand, the process moves on to step S16. In step S16, the detecting unit 74 reads out the developed mid-surgery image stored in the development memory 73 as the pre-degeneration image.

In step S17, the output memory 80 outputs the stored mid-surgery image to the display device 11. As a result, the mid-surgery image is displayed on the display device 11.

The procedures in steps S18 through S20 are similar to the procedures in steps S11 through S13, and therefore, explanation of them is not repeated herein.

In step S21, the detecting unit 74 determines whether the foot switch 26 has been again pressed by the operator or the like. If it is determined in step S21 that the foot switch 26 has not been again pressed, the process moves on to step S22.

In step S22, the output memory 80 outputs the stored mid-surgery image to the display device 11. As a result, the mid-surgery image is displayed on the display device 11. After the procedure in step S22, the process returns to step S18, and the procedures insteps S18 through S22 are repeated until the foot switch 26 is again pressed.

If it is determined in step S21 that the foot switch 26 has been again pressed, on the other hand, the process moves on to step S23. In step S23, the detecting unit 74 reads out the mid-surgery image stored in the development memory 73 as the post-degeneration image.

In step S24, in accordance with changes in color and luminance between the pre-degeneration image and the post-degeneration image, the detecting unit 74 detects the degenerated regions in the post-degeneration image. The detecting unit 74 supplies the identifying unit 75 with feature information such as the shape, the amount of change in luminance, the amount of change in color, the edge pattern, and the texture of each degenerated region, information about the feature points around each degenerated region, location information, and the number of degenerated regions.

In step S25, in accordance with the feature information about each degenerated region and the number of degenerated regions supplied from the detecting unit 74, the identifying unit 75 identifies the degeneration method of the degenerated regions. The identifying unit 75 supplies the information memory 76 with degenerated region information that includes the degenerated region identification information, the degeneration method, the location information, and the shape of each degenerated region, and the number of degenerated regions.

In step S26, the information memory 76 stores the degenerated region information supplied from the identifying unit 75. The information memory 76 reads out the stored degenerated region information, and supplies the degenerated region information to the tracking unit 77. The tracking unit 77 supplies the drawing unit 78 with the degeneration method, the location information, and the shape of each degenerated region, and the number of degenerated regions included in the degenerated region information supplied from the information memory 76.

In step S27, in accordance with the degeneration method, the location information, and the shape of each degenerated region, and the number of degenerated regions supplied from the tracking unit 77, the drawing unit 78 draws a resection line, and generates a resection line image. The drawing unit 78 supplies the resection line image to the drawing memory 79.

In step S28, the drawing memory 79 stores the resection line image supplied from the drawing unit 78. The drawing memory 79 reads out the stored resection line image, and supplies the resection line image to the output memory 80.

In step S29, the output memory 80 writes the resection line image supplied from the drawing memory 79 over the mid-surgery image stored in step S20 or S34, and thus, superimposes the resection line on the mid-surgery image.

In step S30, the output memory 80 outputs the stored mid-surgery image having the resection line superimposed thereon to the display device 11. As a result, the mid-surgery image having the resection line superimposed thereon is displayed on the display device 11.

In step S31, the CCU 12 determines whether the image processing is to be ended, or whether mid-surgery image transmission from the endoscope 19 has been ended, for example. If it is determined in step S31 that the image processing is not to be ended yet, the process moves on to step S32. The procedures in steps S32 through S34 are similar to the procedures in steps S11 through S13, and therefore, explanation of them is not repeated herein.

In step S35, in accordance with the degenerated region identification information and the location information included in the degenerated region information supplied from the information memory 76 in step S26 or S36, the tracking unit 77 detects the degenerated regions in the mid-surgery image supplied from the development memory 73 in step S34. The tracking unit 77 supplies the information memory 76 with degenerated region information about the detected degenerated regions.

In step S36, the information memory 76 updates the stored degenerated region information with the degenerated region information supplied from the tracking unit 77 in step S35. The information memory 76 reads out the updated degenerated region information, and supplies the updated degenerated region information to the tracking unit 77. The process then returns to step S27.

If it is determined in step S31 that the image processing is to be ended, on the other hand, the image processing comes to an end.

As described above, the CCU 12 aids judgment and memory of the operator by drawing a resection line on a mid-surgery image in accordance with the degenerated regions in the mid-surgery image. Thus, the burden on the operator is reduced, and accurate surgical resection can be performed in a shorter time.

Furthermore, even in a case where the operator has poor experience or the like, there is no need to increase the number of degenerated regions in the burning method or the dyeing method. Accordingly, the influence (damage) on the tissue of the abdominal portion 31 of the patient and the burden on the patient can be minimized.

Second Embodiment (Example Configuration of the CCU in a Second Embodiment of an Endoscopic Surgical System)

The configuration of a second embodiment of an endoscopic surgical system to which the present disclosure is applied is the same as the configuration of the endoscopic surgical system 10 shown in FIG. 1, except that the endoscope 19 generates mid-surgery images from more than one viewpoint, and generates a mid-surgery image from one viewpoint and a parallax image, and the CCU has a different configuration. Therefore, only the CCU of the second embodiment will be described below.

Figure 11:
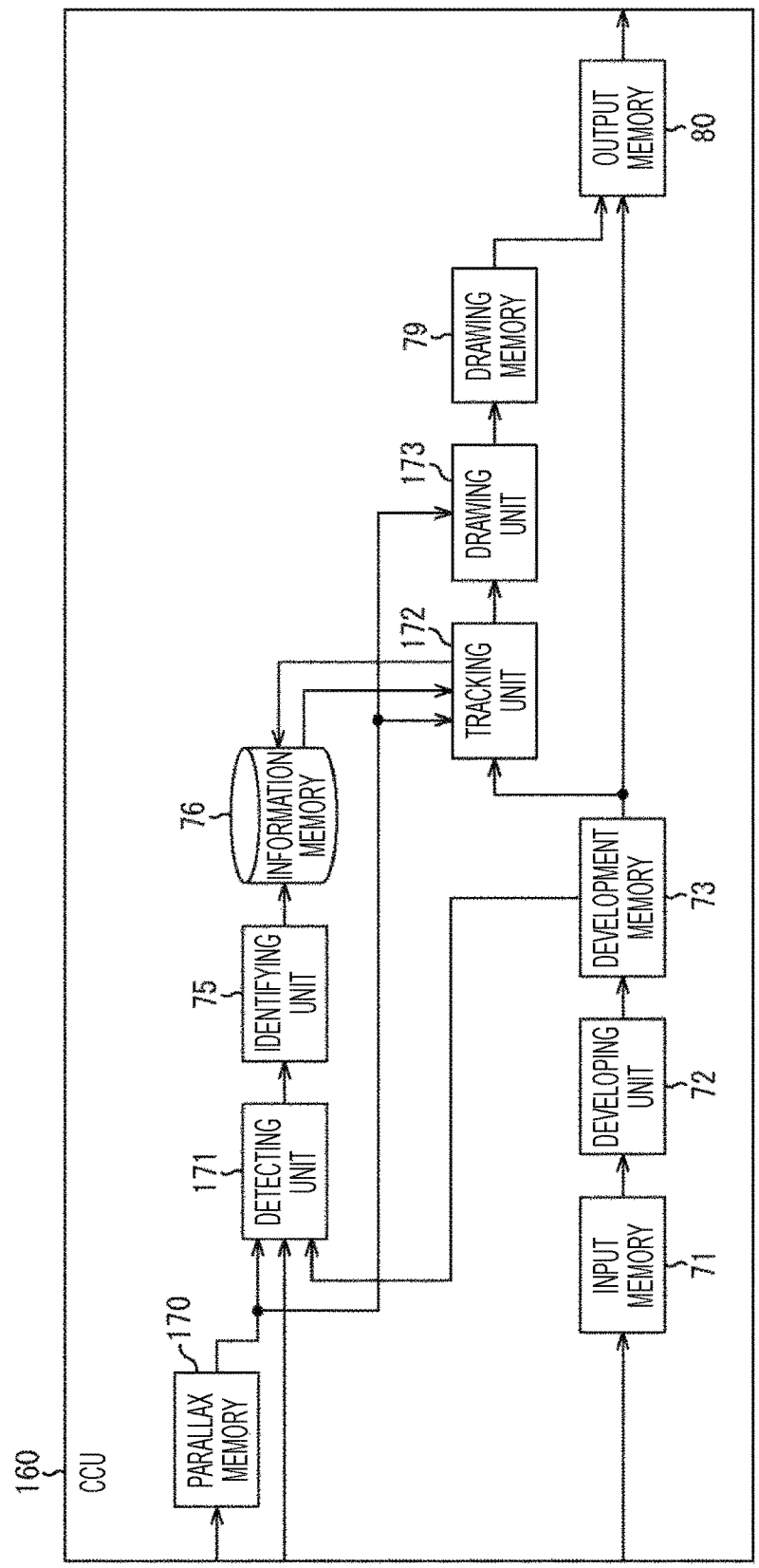
FIG. 11 is a block diagram showing an example configuration of a CCU of a second embodiment of an endoscopic surgical system to which the present disclosure is applied.

FIG. 11 is a block diagram showing an example configuration of the CCU of the second embodiment of an endoscopic surgical system to which the present disclosure is applied.

In the configuration shown in FIG. 11, the same components as those shown in FIG. 2 are denoted by the same reference numerals as those used in FIG. 2. The explanations that have already been made will not be repeated.

The configuration of the CCU 160 shown in FIG. 11 differs from the configuration shown in FIG. 2, in that a parallax memory 170 is newly employed, and the detecting unit 74, the tracking unit 77, and the drawing unit 78 are replaced with a detecting unit 171, a tracking unit 172, and a drawing unit 173.

A parallax image received from the endoscope 19 is input to the parallax memory 170 of the CCU 160, and is stored in the parallax memory 170. It should be noted that a parallax image is an image showing pixel values that are depth values indicating the distances in the depth direction between the endoscope 19 and the object at the respective pixels in a mid-surgery image generated by the endoscope 19.

The detecting unit 171 acquires an operation signal that is supplied from the foot switch 26 and indicates an action of the operator on the foot switch 26 immediately before the start of degeneration. In accordance with this operation signal, the detecting unit 171 reads a mid-surgery image as a pre-degeneration image from the development memory 73.

The detecting unit 171 also acquires an operation signal that is supplied from the foot switch 26 and indicates an action of the operator on the foot switch 26 immediately after the end of the degeneration. In accordance with this operation signal, the detecting unit 171 reads a mid-surgery image as a post-degeneration image from the development memory 73. The detecting unit 171 also reads the parallax image corresponding to the post-degeneration image from the parallax memory 170.

Like the detecting unit 74, in accordance with changes in color and luminance between the pre-degeneration image and the post-degeneration image, the detecting unit 171 detects the degenerated regions in the post-degeneration image. In accordance with the parallax image corresponding to the post-degeneration image, the detecting unit 171 corrects the detected degenerated regions.

For example, the detecting unit 171 deletes regions having depth values greatly differing from those of the surrounding regions among the detected degenerated regions, and adds regions that exist around the detected degenerated regions and have the same depth values as those of the degenerated regions, to the degenerated regions. In this manner, the detecting unit 171 corrects the detected degenerated regions in accordance with the parallax image corresponding to the post-degeneration image. Thus, degenerated region detection accuracy can be increased.

The detecting unit 171 supplies the identifying unit 75 with the feature information, the surrounding feature point information, and the location information about each corrected degenerated region, and the number of degenerated regions.

The tracking unit 172 supplies the drawing unit 173 with the degeneration method, the location information, and the shape of each degenerated region, and the number of degenerated regions included in the degenerated region information supplied from the information memory 76. In accordance with the degenerated region identification information and the location information included in the degenerated region information, the tracking unit 172 also detects the degenerated regions in a mid-surgery image that is supplied from the development memory 73 and is generated later than the mid-surgery image corresponding to the degenerated region information.

The tracking unit 172 reads the parallax image corresponding to the mid-surgery image including the detected degenerated regions from the parallax memory 170. Like the detecting unit 171, in accordance with the read parallax image, the tracking unit 172 corrects the detected degenerated regions. The tracking unit 172 supplies the information memory 76 with degenerated region information about the corrected degenerated regions.

From the parallax memory 170, the drawing unit 173 reads the parallax image corresponding to the information supplied from the tracking unit 172. In accordance with the degeneration method, the location information, and the shape of each degenerated region, and the number of degenerated regions supplied from the tracking unit 172, and the parallax image, the drawing unit 173 draws a resection line and the like, and generates a resection line image.

For example, the drawing unit 173 draws such a resection line as to minimize the resection area, or draws a smooth resection line having small depth value differences. The drawing unit 173 supplies the resection line image to the drawing memory 79.

It should be noted that the output memory 80 in this example supplies the display device 11 only with the mid-surgery image having the resection line superimposed thereon. However, in a case where the display device 11 is formed with a 3D display, the parallax image corresponding to the mid-surgery image is also supplied to the display device 11. In this case, the display device 11 horizontally shifts the mid-surgery image having the resection line superimposed thereon, in accordance with the parallax image. By doing so, the display device 11 converts the single-view 2D mid-surgery image into a multi-view 3D mid-surgery image, and displays the multi-view 3D mid-surgery image.

(Explanation of a Resection Line in a Case where the Degeneration Method is the Burning Method)

Figure 12:
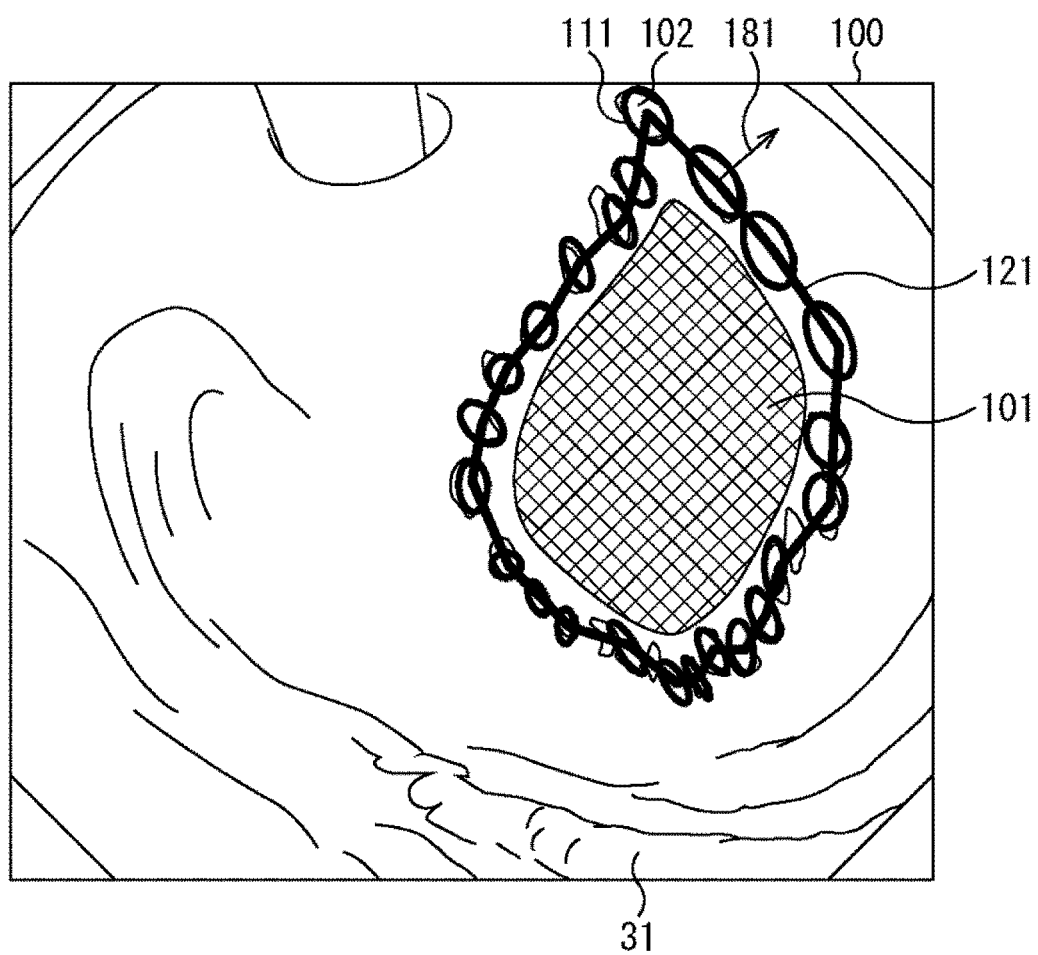
FIG. 12 is a diagram showing an example of a resection line in a case where the degeneration method is the burning method.

FIG. 12 is a diagram showing an example of a resection line in a case where the degeneration method is the burning method.

In FIG. 12, the same parts as those shown in FIG. 5 are denoted by the same reference numerals as those used in FIG. 5, and explanation of them will not be repeated below.

As shown in FIG. 12, in a case where the degeneration method is the burning method, the drawing unit 173 draws a resection line 121 extending through the gravity centers of all the regions 111 in a post-degeneration image 100, like the drawing unit 78. In accordance with the parallax image corresponding to the post-degeneration image 100, the drawing unit 173 also displays normal vectors 181 indicating the angles formed with the planes of the regions 111.

It should be noted that, in accordance with the parallax image corresponding to the post-degeneration image 100, the drawing unit 173 may calculate the total length of the resection line 121, the area of the region surrounded by the resection line 121, or the like before drawing the resection line 121. Also, the drawing unit 173 may change the color or the thickness of the resection line 121, in accordance with the depth values of the pixels on which the resection line 121 is to be drawn.

(Explanation of a Process to be Performed by the CCU)

Figure 13:
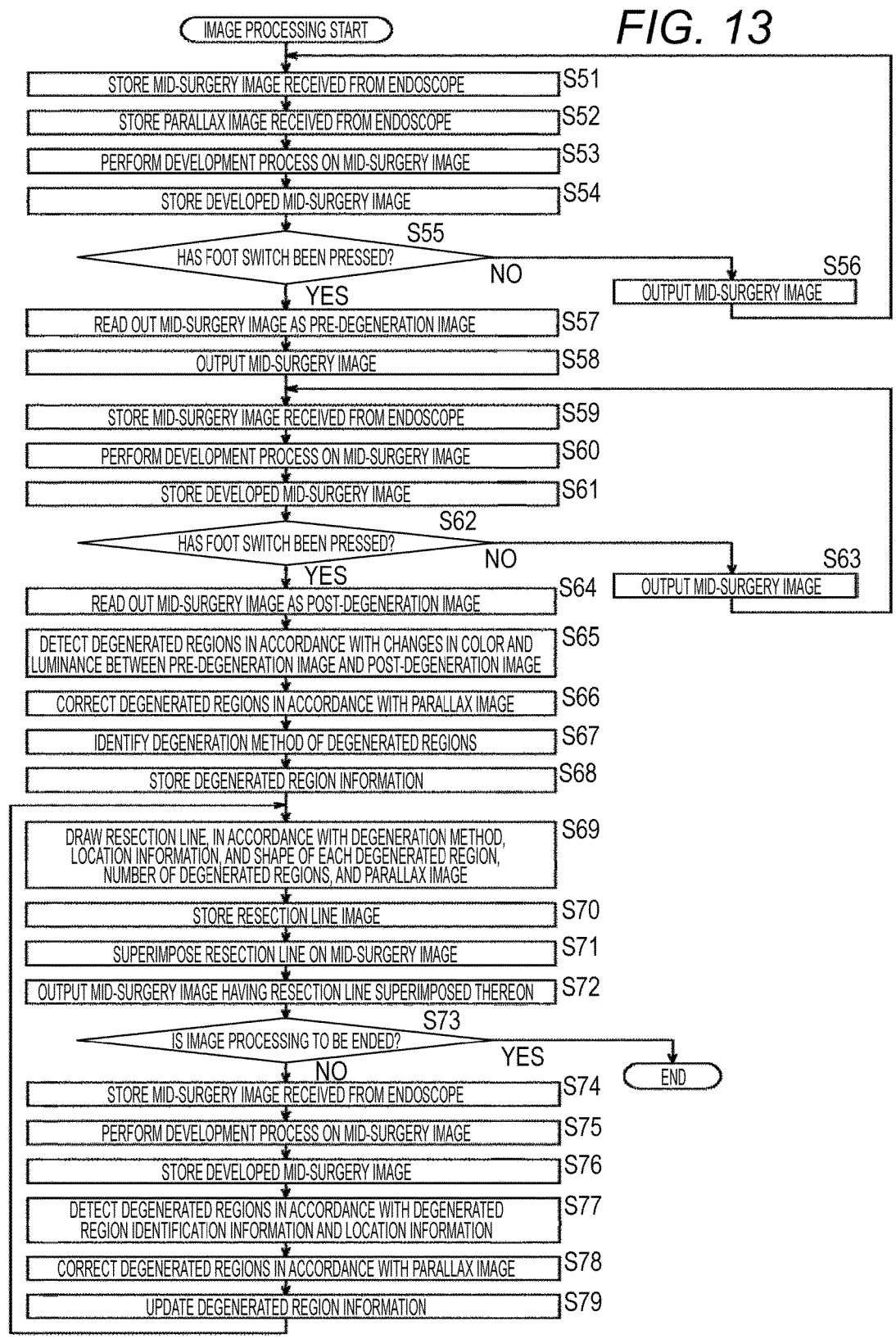
FIG. 13 is a flowchart for explaining image processing to be performed by the CCU shown in FIG. 11.

FIG. 13 is a flowchart for explaining image processing to be performed by the CCU 160 shown in FIG. 11.

In step S51 in FIG. 13, the input memory 71 stores a mid-surgery image received from the endoscope 19. The input memory 71 also reads out the stored mid-surgery image, and supplies the mid-surgery image to the developing unit 72.

In step S52, the parallax memory 170 stores the parallax image received together with the mid-surgery image from the endoscope 19.

The procedures in steps S53 through S65 are similar to the procedures in steps S12 through S24 in FIG. 10, and therefore, explanation of them is not repeated herein.

In step S66, the detecting unit 171 detects the parallax image corresponding to the post-degeneration image from the parallax memory 170, and, in accordance with the parallax image, corrects the degenerated regions detected in step S65. The detecting unit 171 supplies the identifying unit 75 with the feature information, the surrounding feature point information, and the location information about each corrected degenerated region, and the number of degenerated regions.

The procedures in steps S67 and S68 are similar to the procedures in steps S25 and S26 in FIG. 10, and therefore, explanation of them is not repeated herein.

In step S69, in accordance with the degeneration method, the location information, and the shape of each degenerated region, and the number of degenerated regions supplied from the tracking unit 172, and the parallax image that corresponds to these pieces of information and is read from the parallax memory 170, the drawing unit 173 draws a resection line, and generates a resection line image. The drawing unit 173 supplies the resection line image to the drawing memory 79.

The procedures in steps S70 through S77 are similar to the procedures in steps S28 through S35 in FIG. 10, and therefore, explanation of them is not repeated herein.

In step S78, the tracking unit 172 reads the parallax image corresponding to the degenerated regions detected in step S77 from the parallax memory 170, and, in accordance with the parallax image, corrects the degenerated regions. The tracking unit 172 supplies the information memory 76 with degenerated region information about the corrected degenerated regions.

In step S79, the information memory 76 updates the stored degenerated region information with the degenerated region information supplied from the tracking unit 172 in step S78. The information memory 76 reads out the updated degenerated region information, and supplies the updated degenerated region information to the tracking unit 172. The process then returns to step S69.

It should be noted that, although a resection line is drawn in accordance with information included in a mid-surgery image and a parallax image in the second embodiment, a resection line may be drawn in accordance with information other than a mid-surgery image and a parallax image.

For example, a resection line may be drawn in accordance with a mid-surgery image and information obtained from a medical image generated by a medical device such as a computed tomography (CT) device, a magnetic resonance imaging (MRI) device, or an ultrasound diagnostic device, before or during surgery.

In this case, a resection line can be drawn so as to avoid blood vessels, pipes, nerves, and the like that exist below the tissue surface of the abdominal portion 31 and are difficult to spot in a mid-surgery image, for example. It is also possible to highlight a resection line to which close attention should be paid at the time of resection because the resection line exists near blood vessels, pipes, or nerves, by changing the color or increase the thickness of the resection line, or causing the resection line to blink.

Also, in a case where it is not possible to prevent a resection line from intersecting a blood vessel, the resection line that intersects the blood vessel can be drawn, and the amount of resection-caused bleeding can be estimated from the thickness and the pulsation of the blood vessel, and be drawn together with the resection line. Further, in a case where it is not possible to prevent a resection line from intersecting a blood vessel, the resection line can be drawn so that the total amount of resection-caused bleeding estimated from the thickness and the pulsation of the blood vessel is minimized.

<Explanation of a Superimposing Method>

Figure 14:
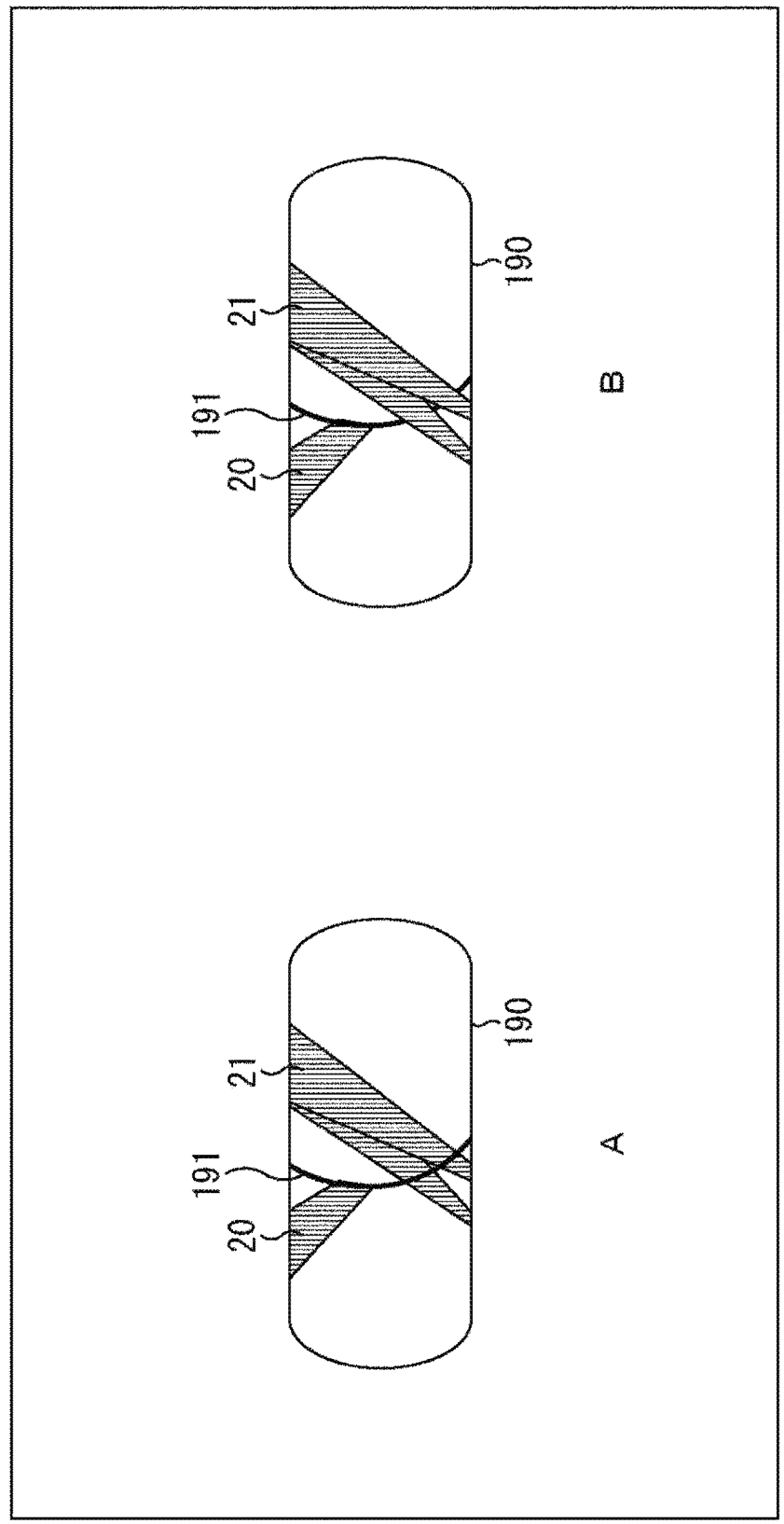
FIG. 14 is a diagram for explaining a method of resection line superimposition to be performed by an output memory.
Figure 15:
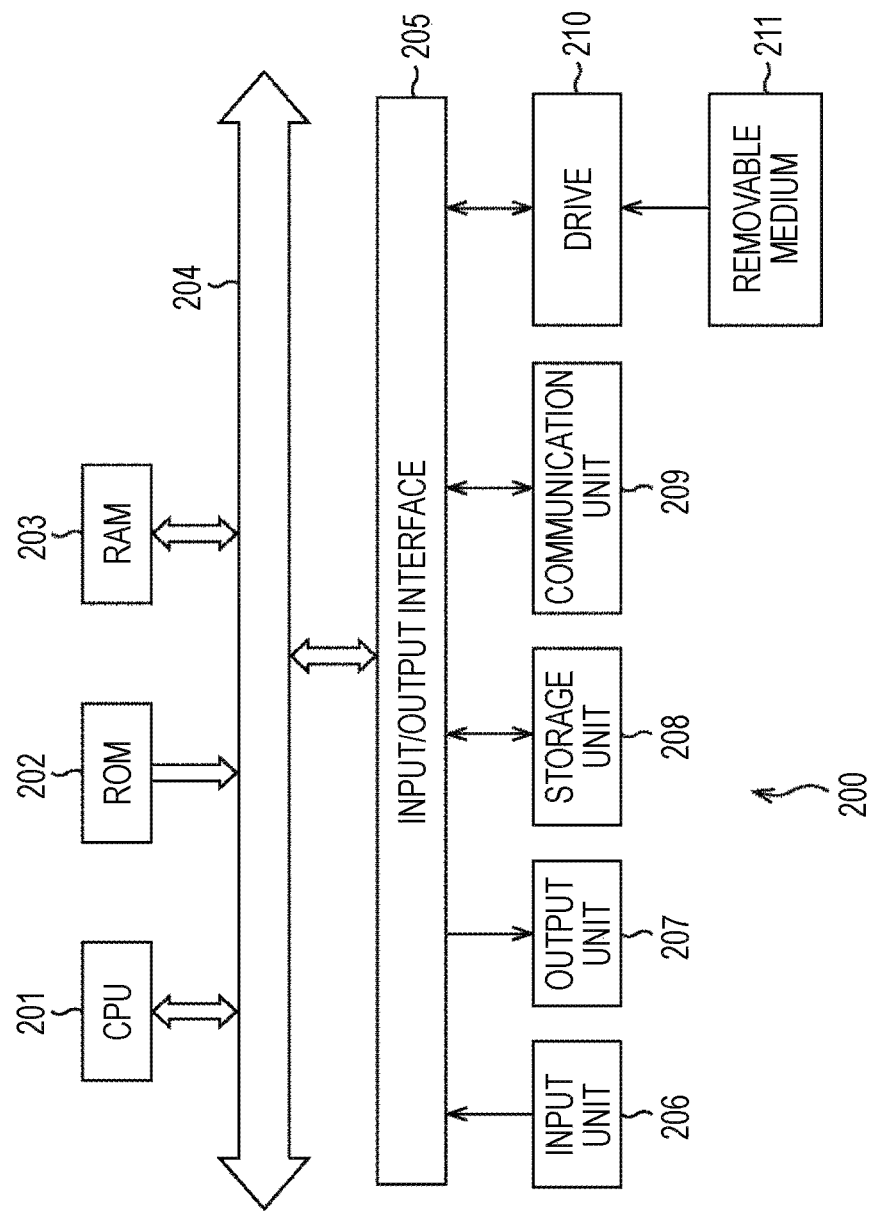
FIG. 15 is a block diagram showing an example configuration of the hardware of a computer.

FIG. 14 is a diagram for explaining a method of resection line superimposition to be performed by the output memory 80.

In the above description, the output memory 80 superimposes a resection line on a mid-surgery image by writing a resection line image over the mid-surgery image. Therefore, even in a case where a mid-surgery image 190 includes images of surgical tools such as the energetic treatment tool 20 and the forceps 21, a resection line 191 is written over the images of the energetic treatment tool 20 and the forceps 21, as shown in A of FIG. 14. As a result, if the forceps 21 cross the resection line 191 as shown in A of FIG. 14, the resection line 191 obstructs the view, and might hinder the surgical procedure.

Therefore, the output memory 80 may not write a resection line image over the images of the energetic treatment tool 20 and the forceps 21 in the mid-surgery image. In that case, the resection line 191 is not drawn on the image of the forceps 21 in the mid-surgery image 190, as shown in B of FIG. 14.

Specifically, the CCU 12 or the CCU 160 recognizes images of the energetic treatment tool 20 and the forceps 21 from a mid-surgery image output from the development memory 73, or performs color identification using the color information about the energetic treatment tool 20 and the forceps 21, for example. In this manner, the CCU 12 or the CCU 160 detects the energetic treatment tool 20 and the forceps 21 in a mid-surgery image. It should be noted that the CCU 160 may be designed to detect the energetic treatment tool 20 and the forceps 21 in a mid-surgery image in accordance with a parallax image.

At the time of superimposition of the resection line 191 by the output memory 80, the CCU 12 or the CCU 160 prohibits superimposition of the resection line 191 on the energetic treatment tool 20 and the forceps 21 in a mid-surgery image, in accordance with detection information indicating the detected locations or the like of the energetic treatment tool 20 and the forceps 21 in the mid-surgery image. As described above, display of images of the energetic treatment tool 20 and the forceps 21 to be used in the surgical procedure is given priority over display of a resection line, so that the operator can easily carry out the surgical procedure.

<Explanation of a Computer>

The above-described series of processes of the CCUs 12 and 160 can be performed by hardware or by software. In a case where the series of processes are to be performed by software, the program that forms the software is installed into a computer. Here, the computer may be a computer incorporated into special-purpose hardware, or may be, for example, a general-purpose personal computer, and the like, that can execute various kinds of functions, having various kinds of programs installed thereinto.

FIG. 15 is a block diagram showing an example configuration of the hardware of a computer that performs the above described series of processes of the CCUs 12 and 160 in accordance with a program.

In a computer 200, a central processing unit (CPU) 201, a read only memory (ROM) 202, and a random access memory (RAM) 203 are connected to one another through a bus 204.

An input/output interface 205 is further connected to the bus 204. An input unit 206, an output unit 207, a storage unit 208, a communication unit 209, and a drive 210 are connected to the input/output interface 205.

The input unit 206 is formed with a keyboard, a mouse, a microphone, operation buttons, a connecting unit of a camera cable, and the like. The output unit 207 is formed with a display, a speaker, and the like. The storage unit 208 is formed with a hard disk, a nonvolatile memory, or the like. The communication unit 209 is formed with a network interface or the like. The drive 210 drives a removable medium 211, such as a magnetic disk, an optical disk, a magnetooptical disk, or a semiconductor memory.

In the computer 200 having the above described configuration, the CPU 201 loads a program stored in the storage unit 208 into the RAM 203 via the input/output interface 205 and the bus 204, for example, and executes the program, so that the above described series of processes are performed.

The program to be executed by the computer 200 (the CPU 201) may be recorded on the removable medium 211 as a package medium to be provided, for example. Alternatively, the program can be provided via a wired or wireless transmission medium, such as a local area network, the Internet, or digital satellite broadcasting.

In the computer 200, the program can be installed into the storage unit 208 via the input/output interface 205 when the removable medium 211 is mounted on the drive 210. The program can also be received by the communication unit 209 via a wired or wireless transmission medium, and be installed into the storage unit 208. Also, the program may be installed beforehand into the ROM 202 or the storage unit 208.

It should be noted that the program to be executed by the computer 200 may be a program for performing processes in chronological order in accordance with the sequence described in this specification, or may be a program for performing processes in parallel or performing a process when necessary, such as when there is a call.

Also, in this specification, a system means an assembly of components (devices, modules (parts), and the like), and not all the components need to be provided in the same housing.

In view of this, devices that are housed in different housings and are connected to one another via a network form a system, and one device having modules housed in one housing is also a system.

Further, the advantageous effect described in this specification is merely an example, and the advantageous effects of the present technology are not limited to it and may include other effects.

Also, embodiments of the present disclosure are not limited to the above described embodiments, and various modifications may be made to them within the scope of the present disclosure.

For example, the CCUs 12 and 160 may store a mid-surgery image and a parallax image, and perform image processing on the stored mid-surgery image and parallax image, instead of performing real-time image processing on a mid-surgery image and a parallax image transmitted from the endoscope 19. In this case, for example, it is possible to perform a laparoscopic operation in a simulative manner for an educational purpose or the like.

Also, in detecting degenerated regions and identifying a degeneration method, additional information such as the type of the current organ on which the surgery is to be performed, the purpose of the surgery or the test, the surgical procedures, and the patient information may be used to increase accuracy and robustness.

Further, the output memory 80 may control execution/non-execution of superimposition of a resection line, in accordance with an action of the operator or the like on the foot switch 26. Meanwhile, a parallax image may be generated by the CCU 160 using mid-surgery images generated by the endoscope 19 from different viewpoints.

The light source device 13 may be a white light source, or may be a special light source for fluorescent observation.

Further, the degeneration method may be a method for changing the color of an affected area to a fluorescent color by injection of a fluorescent specimen, a method by which tape is applied along a resection line at intervals, or the like. The auxiliary information may not be formed with a resection line image, as long as the operator can recognize the resection line from the auxiliary information. For example, in a case where the degeneration method is a method for changing the color of an affected area to a fluorescent color through injection of a fluorescent specimen, an image indicating the degenerated regions in a predetermined color in a mid-surgery image may be used as the auxiliary information.

Further, the CCU 12 may detect the location of a surgical tool such as the forceps 21 from a mid-surgery image, or the like. If the forceps 21 or the like move away from the resection line, the CCU 12 may cause the screen of the display device 11 to display an alarm to facilitate the operator's attention to the detachment, or may sound the alarm.

The present disclosure may be applied not only to systems for surgery, but also to systems for testing and observation.

It should be noted that the present disclosure may also be embodied in the configurations described below.

(1)
An image processing device including:
an identifying unit that identifies the type of tissue degeneration in a mid-surgery image; and
a drawing unit that draws auxiliary information for an operator in accordance with the identified type of the tissue degeneration, the auxiliary information being to be superimposed on the mid-surgery image.

(2)
The image processing device of (1), in which the drawing unit draws a line in accordance with the identified type of the tissue degeneration.

(3)
The image processing device of (2), in which the drawing unit draws the line extending through a plurality of portions of the tissue degeneration in the mid-surgery image.

(4)
The image processing device of (2), in which the drawing unit draws the line indicating the contour of the tissue degeneration in the mid-surgery image.

(5)
The image processing device of any of (1) to (4), in which the identifying unit identifies the type of the tissue degeneration in accordance with feature information about a degenerated region of the tissue degeneration and the number of the degenerated regions.

(6)
The image processing device of (5), in which, in a case where the number of the degenerated regions is larger than one, the identifying unit determines the tissue degeneration to be degeneration caused by a burning method.

(7)
The image processing device of (5), in which, in a case where the number of the degenerated regions is one, the identifying unit determines the tissue degeneration to be degeneration caused by a discoloring method.

(8)
The image processing device of any of (1) to (7), in which the drawing unit draws the auxiliary information for the operator in accordance with a degenerated region of the tissue degeneration and a parallax image corresponding to the mid-surgery image.

(9)
The image processing device of any of (1) to (8), further including
a detecting unit that detects the tissue degeneration in the mid-surgery image generated after the tissue degeneration occurs, in accordance with the mid-surgery image generated before the tissue degeneration occurs and the mid-surgery image generated after the tissue degeneration occurs,
in which the drawing unit draws the auxiliary information for the operator in accordance with the tissue degeneration detected by the detecting unit.

(10)
The image processing device of (9), further including
a tracking unit that tracks temporal changes in the tissue degeneration in the mid-surgery image generated after the tissue degeneration occurs, in accordance with information about the tissue degeneration detected by the detecting unit,
in which the drawing unit causes temporal changes in the auxiliary information for the operator, in accordance with the temporal changes tracked by the tracking unit.

(11)
The image processing device of (9) or (10), in which the detecting unit corrects the detected tissue degeneration in accordance with a parallax image corresponding to the mid-surgery image generated after the tissue degeneration occurs.

(12)
The image processing device of any of (1) to (11), in which the drawing unit draws the auxiliary information for the operator in accordance with information obtained from an image further generated by a medical device before or during surgery.

(13)

The image processing device of any of (1) to (12), in which the drawing unit draws the auxiliary information for the operator in accordance with detection information about a surgical tool in the mid-surgery image.

(14)

An image processing method including:

an identifying step of identifying the type of tissue degeneration in a mid-surgery image; and a drawing step of drawing auxiliary information for an operator in accordance with the identified type of the tissue degeneration, the auxiliary information being to be superimposed on the mid-surgery image, the identifying step and the drawing step being carried out by an image processing device.

(15)

A surgical system including:

a treatment device that degenerates the current object on which surgery is to be performed;

an imaging device that generates a mid-surgery image of the current object; and an image processing device that performs image processing on the mid-surgery image, in which the image processing device includes:

an identifying unit that identifies the type of tissue degeneration in the mid-surgery image; and a drawing unit that draws auxiliary information for an operator in accordance with the identified type of the tissue degeneration, the auxiliary information being to be superimposed on the mid-surgery image.

REFERENCE SIGNS LIST

10 Endoscopic surgical system
12 CCU
19 Endoscope
20 Energetic treatment tool
74 Detecting unit
75 Identifying unit
77 Tracking unit
78 Drawing unit
121, 153 Resection line
173 Drawing unit

The invention claimed is:

1. An image processing device comprising:
processing circuitry configured to
identify a type of tissue degeneration in a mid-surgery image in accordance with feature information regarding at least one degenerated region of the mid-surgery image,
draw auxiliary information for an operator based on the identified type of the tissue degeneration, the auxiliary information being displayed on the mid-surgery image, wherein,
when the feature information indicates the at least one degenerated region is a plurality of discontinuous degenerated regions, the tissue degeneration is identified as caused by a burn and the drawn auxiliary information is based on locations of the plurality of discontinuous degenerated regions, and,
when the feature information indicates the at least one degenerated region is a single continuous degenerated region, the tissue degeneration is identified as caused by a discoloring and the drawn auxiliary information is based on a contour of the single continuous degenerated region.

2. The image processing device according to claim 1, wherein the drawn auxiliary information is a line drawn in accordance with the identified type of the tissue degeneration.

3. The image processing device according to claim 2, wherein the line drawn in accordance with the identified type of the tissue degeneration is a line extending through the locations of the plurality of discontinuous degenerated regions.

4. The image processing device according to claim 2, wherein the line drawn in accordance with the identified type of the tissue degeneration is based on the contour of the single continuous degenerated region.

5. The image processing device according to claim 1, wherein the processing circuitry is further configured to
draw the auxiliary information for the operator in accordance with the at least one degenerated region of the tissue degeneration and a parallax image corresponding to the mid-surgery image.

6. The image processing device according to claim 1, wherein the processing circuitry is further configured to
detect the at least one degenerated region of the tissue degeneration in the mid-surgery image based on a pre-degeneration mid-surgery image and a mid-surgery image generated after the tissue degeneration occurs, and
draw the auxiliary information for the operator in accordance with the detected at least one degenerated region of the tissue degeneration.

7. The image processing device according to claim 6, wherein the processing circuitry is further configured to
track temporal changes in the detected at least one degenerated region of the tissue degeneration in the mid-surgery image, and
update, intraoperatively, the auxiliary information drawn for the operator based on the tracked temporal changes in the detected at least one degenerated region of the tissue degeneration.

8. The image processing device according to claim 6, wherein the processing circuitry is further configured to
correct the detected at least one degenerated region of the tissue degeneration in accordance with a parallax image corresponding to the mid-surgery image generated after the tissue degeneration occurs.

9. The image processing device according to claim 1, wherein the processing circuitry is further configured to
draw the auxiliary information for the operator in accordance with information obtained from an image generated by a medical device before or during surgery.

10. The image processing device according to claim 1, wherein the processing circuitry is further configured to
draw the auxiliary information for the operator in accordance with detection information about a surgical tool in the mid-surgery image.

11. An image processing method comprising:
identifying, by processing circuitry, a type of tissue degeneration in a mid-surgery image in accordance with feature information regarding at least one degenerated region of the mid-surgery image; and
drawing, by the processing circuitry, auxiliary information for an operator based on the identified type of the tissue degeneration, the auxiliary information being displayed on the mid-surgery image, wherein, when the feature information indicates the at least one degenerated region is a plurality of discontinuous degenerated regions, the tissue degeneration is identified as caused by a burn and the drawn auxiliary information is based on locations of the plurality of discontinuous degenerated regions, and, when the feature information indicates the at least one degenerated region is a single continuous degenerated region, the tissue degeneration is identified as caused by a discoloring and the drawn auxiliary information is based on a contour of the single continuous degenerated region.

12. A surgical system comprising:
a treatment device configured to degenerate a current object on which surgery is to be performed;
an imaging device configured to generate a mid-surgery image of the current object; and
an image processing device configured to perform image processing on the mid-surgery image, the image processing device including processing circuitry configured to identify a type of tissue degeneration in the mid-surgery image in accordance with feature information regarding at least one degenerated region of the mid-surgery image; and
draw auxiliary information for an operator based on the identified type of the tissue degeneration, the auxiliary information being displayed on the mid-surgery image, wherein,
when the feature information indicates the at least one degenerated region is a plurality of discontinuous degenerated regions, the tissue degeneration is identified as caused by a burn and the drawn auxiliary information is based on locations of the plurality of discontinuous degenerated regions, and,
when the feature information indicates the at least one degenerated region is a single continuous degenerated region, the tissue degeneration is identified as caused by a discoloring and the drawn auxiliary information is based on a contour of the single continuous degenerated region.

* * * * *